(12) United States Patent
Baker et al.

(10) Patent No.: US 8,372,087 B2
(45) Date of Patent: Feb. 12, 2013

(54) MEDICAL DEVICE FIXATION TOOL AND METHOD OF FIXATION OF A MEDICAL DEVICE

(75) Inventors: Randal S. Baker, Ada, MI (US); James A. Foote, Ada, MI (US); Frederick J. Walburn, Grand Rapids, MI (US); Peter M. Wilson, Killingworth, CT (US); Adam I. Lehman, Northford, CT (US); Bryan J. Roodvoets, Caledonia, MI (US)

(73) Assignee: BFKW, LLC, Grand Rapids, MI (US)

( * ) Notice: Subject to any disclaimer, the term of this patent is extended or adjusted under 35 U.S.C. 154(b) by 527 days.

(21) Appl. No.: 12/541,567

(22) Filed: Aug. 14, 2009

(65) Prior Publication Data

US 2010/0063518 A1    Mar. 11, 2010

Related U.S. Application Data

(63) Continuation-in-part of application No. PCT/US2008/053962, filed on Feb. 14, 2008.

(60) Provisional application No. 61/107,511, filed on Oct. 22, 2008, provisional application No. 60/921,930, filed on Apr. 5, 2007, provisional application No. 60/901,457, filed on Feb. 14, 2007.

(51) Int. Cl.
*A61B 17/10* (2006.01)

(52) U.S. Cl. ....................................................... 606/139

(58) Field of Classification Search ................... 606/139, 606/144, 148–150, 153, 205–209; 623/1.11, 623/2.11; 227/175.1
See application file for complete search history.

(56) References Cited

U.S. PATENT DOCUMENTS

| | | | |
|---|---|---|---|
| 5,507,755 A | 4/1996 | Gresl et al. | |
| 5,741,279 A | 4/1998 | Gordon et al. | |
| 6,312,437 B1 * | 11/2001 | Kortenbach | 606/139 |
| 6,398,802 B1 * | 6/2002 | Yee | 623/1.13 |
| 6,447,533 B1 * | 9/2002 | Adams | 606/213 |
| 6,736,828 B1 * | 5/2004 | Adams et al. | 606/213 |
| 6,800,081 B2 * | 10/2004 | Parodi | 606/139 |
| 6,916,332 B2 * | 7/2005 | Adams | 606/219 |
| 7,083,630 B2 | 8/2006 | DeVries et al. | |
| 7,449,024 B2 * | 11/2008 | Stafford | 606/144 |
| 7,704,264 B2 * | 4/2010 | Ewers et al. | 606/151 |

(Continued)

FOREIGN PATENT DOCUMENTS

| | | |
|---|---|---|
| WO | 0135834 A1 | 5/2001 |
| WO | 0185034 A1 | 11/2001 |

(Continued)

OTHER PUBLICATIONS

International Search Report and Written Opinion of the International Searching Authority from corresponding Patent Cooperation Treaty (PCT) Patent Application No. PCT/US08/53962, mailed Aug. 8, 2008.

(Continued)

*Primary Examiner* — Corrine M McDermott
*Assistant Examiner* — Todd J Scherbel
(74) *Attorney, Agent, or Firm* — Gardner, Linn, Burkhart & Flory, LLP

(57) ABSTRACT

A device fixation tool and method of fixation of a medical device within a hollow organ or cavity through a natural orifice includes providing a needle driver and a shaft. The needle driver is adapted for use with at least one needle. At least a portion of the needle driver is positioned with the shaft at a hollow organ or cavity through the natural orifice. Sufficient force is transmitted with the needle driver to the at least one needle to penetrate mammalian tissue and a portion of the medical device.

31 Claims, 33 Drawing Sheets

U.S. PATENT DOCUMENTS

| | | | |
|---|---|---|---|
| 2004/0087976 A1* | 5/2004 | DeVries et al. | 606/142 |
| 2005/0004582 A1* | 1/2005 | Edoga et al. | 606/139 |
| 2005/0251165 A1* | 11/2005 | Vaughan et al. | 606/153 |
| 2005/0251176 A1 | 11/2005 | Swanstrom et al. | |
| 2006/0253131 A1 | 11/2006 | Wolniewicz, III | |
| 2007/0198035 A1* | 8/2007 | Threlkeld | 606/148 |
| 2008/0015633 A1* | 1/2008 | Abbott et al. | 606/207 |

FOREIGN PATENT DOCUMENTS

| | | |
|---|---|---|
| WO | 02060328 A1 | 8/2002 |
| WO | 02094105 A2 | 11/2002 |

OTHER PUBLICATIONS

Commonly assigned U.S. Appl. No. 12/539,112, filed Aug. 11, 2009.

International Preliminary Report on Patenatibility and Written Opinion of the International Searching Authority from corresponding Patent Cooperation Treaty (PCT) Patent Application No. PCT/US08/53962, mailed Aug. 27, 2009.

\* cited by examiner

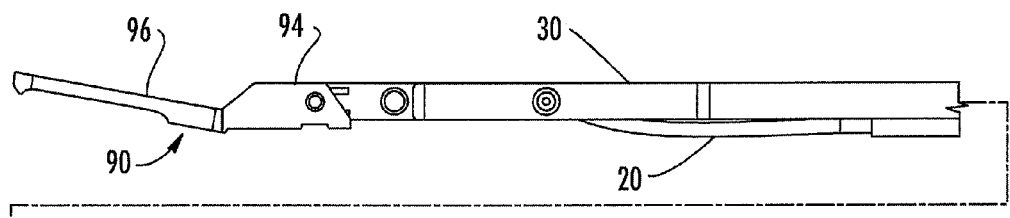
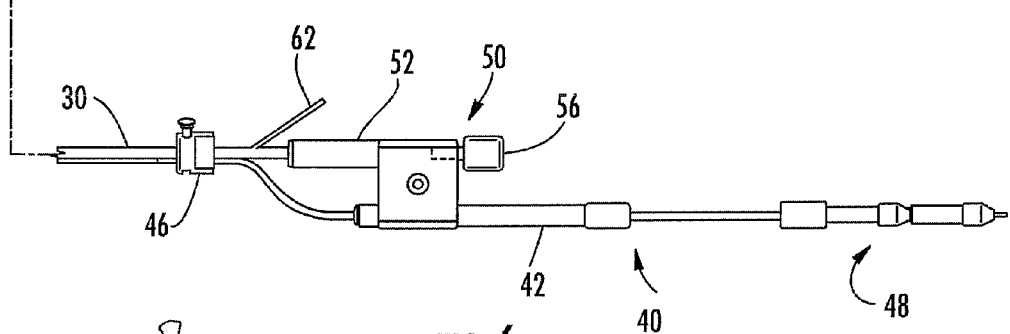
FIG. 6
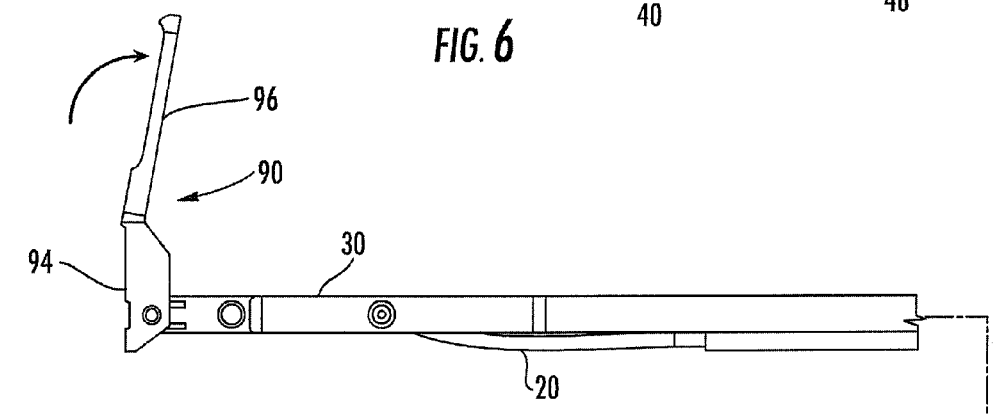
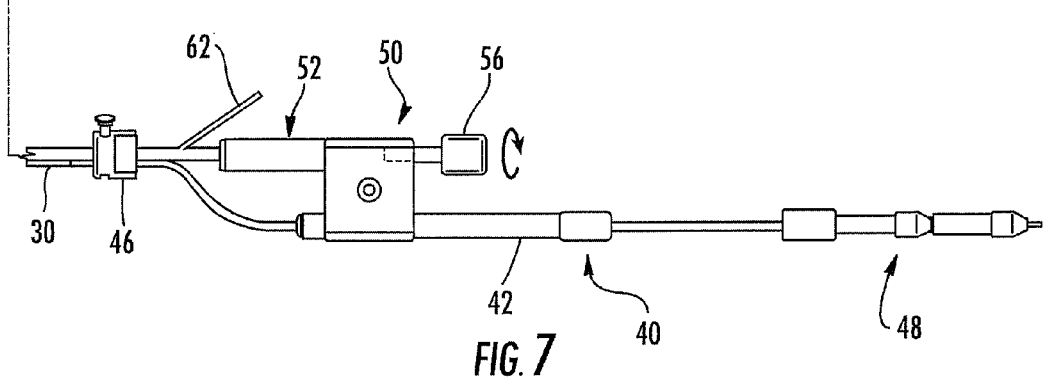
FIG. 7

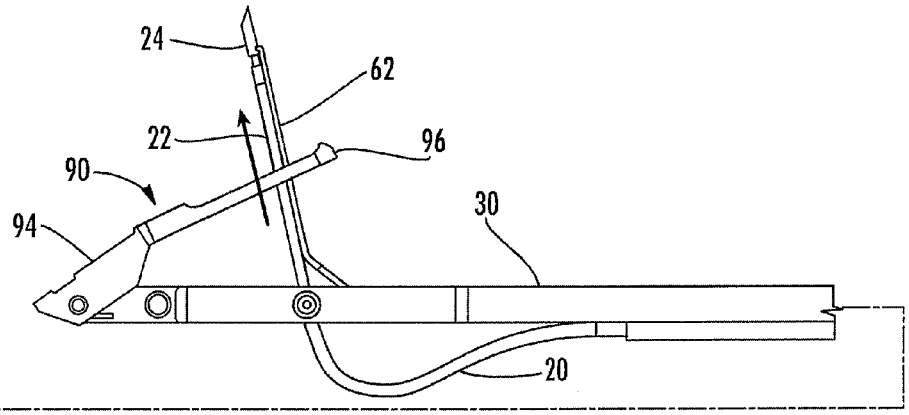
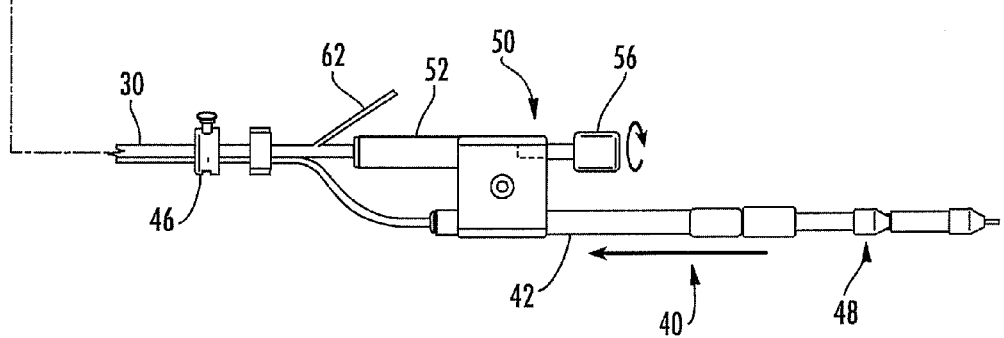
FIG. 10
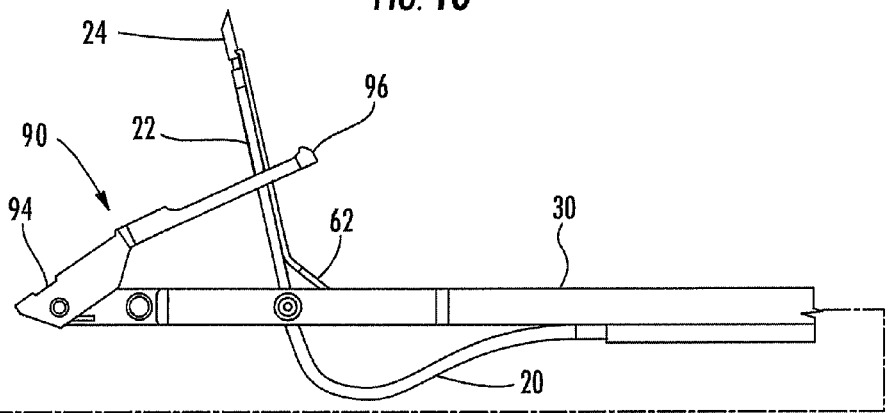
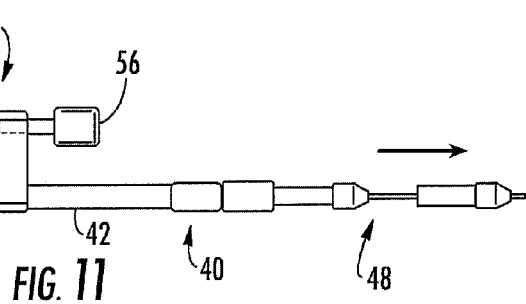
FIG. 11

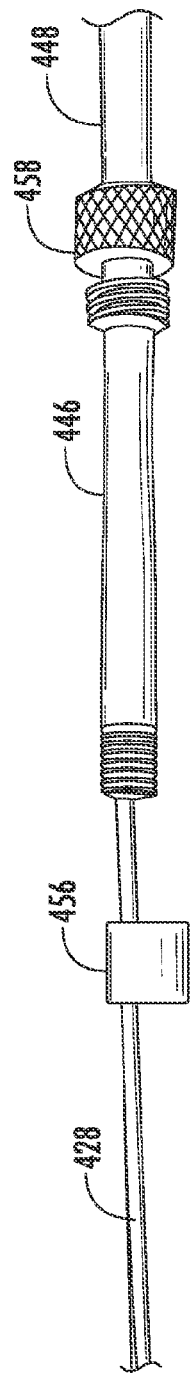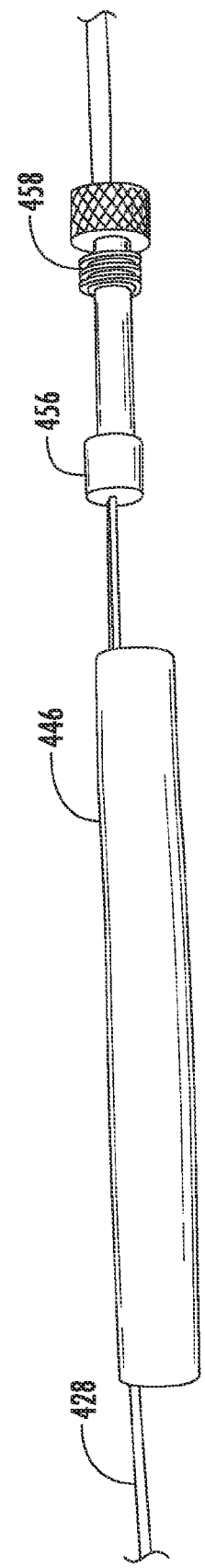

MEDICAL DEVICE FIXATION TOOL AND METHOD OF FIXATION OF A MEDICAL DEVICE

CROSS REFERENCE TO RELATED APPLICATIONS

This application claims priority from U.S. provisional patent application Ser. No. 61/107,511, filed on Oct. 22, 2008, and is a continuation-in-part of International Patent Cooperation Treaty Application No. PCT/US08/53962, filed on Feb. 14, 2008, which claims priority from U.S. provisional patent application Ser. No. 60/901,457, filed on Feb. 14, 2007, and U.S. provisional patent application Ser. No. 60/921,930, filed on Apr. 5, 2007, the disclosures of which are hereby incorporated herein by reference in their entireties.

BACKGROUND OF THE INVENTION

The present invention is directed to a medical device fixation tool and a method of fixation of a medical device and, in particular, to a technique to fix a medical device within a hollow organ or cavity through a natural orifice.

In the course of treating patients for a variety of different maladies and diseases, it sometimes becomes necessary to fix medical devices within the body. As with any procedure, it is desirable to minimize the invasiveness of surgery by avoiding, whenever possible, incisions into the skin or exposure of internal organs. Such minimization not only reduces the patient's recovery time and the substantial costs associated with extended hospital stays, but also greatly diminishes the possibility of complications, such as infection or rejection by the body of a foreign element.

SUMMARY OF THE INVENTION

The present invention provides a medical tool and method for use within the body that can be performed through a natural orifice. This can be accomplished in a minimally invasive manner.

A medical tool and method of fixation for use within a hollow organ or cavity through a natural orifice, according to an aspect of the invention, includes providing a needle driver and a shaft. The needle driver is adapted for use with at least one needle. At least a portion of the needle driver is positioned with the shaft at a hollow organ or cavity through the natural orifice. Sufficient force is transmitted with the needle driver to the at least one needle to penetrate mammalian tissue.

Sufficient force may be transmitted with the needle driver to also penetrate a portion of a medical device to fix the medical device within the hollow organ or cavity. The portion of the medical device may have a greater puncture resistance than the mammalian tissue.

A support may be provided to resist distal movement of the portion of the medical device in response to the force of penetrating that portion of the medical device. The shaft may position the support at a side of the portion of the medical device opposite from said needle driver. The support may further define a first portion and a second portion, the first portion being adjacent the shaft and the second portion defining a central void. The second portion may be moveable from a deployment position to a use position, wherein said central void is substantially aligned with the needle driver in the use position. The second portion may be substantially aligned with said shaft in the deployment position. In the deployment position the support may extend from the shaft or be substantially aligned with the shaft. The support may be pivotally supported at the shaft. A support actuator may be provided to move the support between the use and deployment positions. The actuator may be at an end portion of the shaft opposite the support.

The needle driver may be aimable relative to the shaft. The needle driver may include a needle guide and a needle pusher assembly that is moveable along the needle guide. The needle guide may be aimable relative to the shaft. The needle guide may further include a pusher housing affixed to the shaft, a rotatable yoke fixed to the shaft and a pusher tube. The pusher tube may be slideable proximally in the pusher housing and terminated distally at the rotatable yoke. In this manner, the needle guide may be aimable by adjusting a portion of the pusher tube extending from the pusher housing. The needle guide may be moveable between a deployment position and a use position. The needle guide may be substantially parallel to the shaft in the deployment position and at an angle to the shaft in the use position.

The needle pusher assembly may include a needle deployment tube and a needle deployment filament that is moveable within the needle deployment tube. The needle deployment tube and the needle deployment filament may move together to drive the needle and move relative to each other to deploy the driven needle. A needle may be combined with the needle pusher assembly. The needle may deploy a fastener attached to a tether. A needle driver actuator may be provided to actuate the needle driver to drive a needle through the portion of the medical device. The needle driver actuator may be at an end portion of the shaft opposite the support.

The portion of the needle driver positioned with the shaft at a hollow organ or cavity through the natural orifice may include at lease one opening defined at a distal end of the shaft. The needle driver may include an elongated member having a distal needle that is adapted to enter the at least one opening to penetrate the portion of the medical device. The at least one opening may include a plurality of openings being at different angles relative to the shaft. In this manner, the needle driver may be aimable by entering a selected one of said openings.

The needle driver may transmit sufficient force to the at least one needle to penetrate at least two portions of the medical device. Each of said portions of the medical device may have a greater puncture resistance than mammalian tissue.

The medical device fixation tool may be used to fix medical devices, such as esophageal stents, bariatric devices, anti-reflux devices, nasal gastric tubes, intestinal sleeves, and the like.

These and other objects, advantages, and features of this invention will become apparent upon review of the following specification in conjunction with the drawings.

BRIEF DESCRIPTION OF THE DRAWINGS

FIG. 6 is a side elevation of a medical device fixation tool with the support distally extended;

FIG. 7 is the same view as FIG. 6 with the support in a partially deployed position;

FIG. 10 is the same view as FIG. 9 with the needle deployment tube in a use position;

FIG. 11 is the same view as FIG. 10 with the needle deployed;

FIGS. 40-43 are exploded perspective views of the plunger illustrated in FIG.

DESCRIPTION OF THE PREFERRED EMBODIMENT

Figure 1:
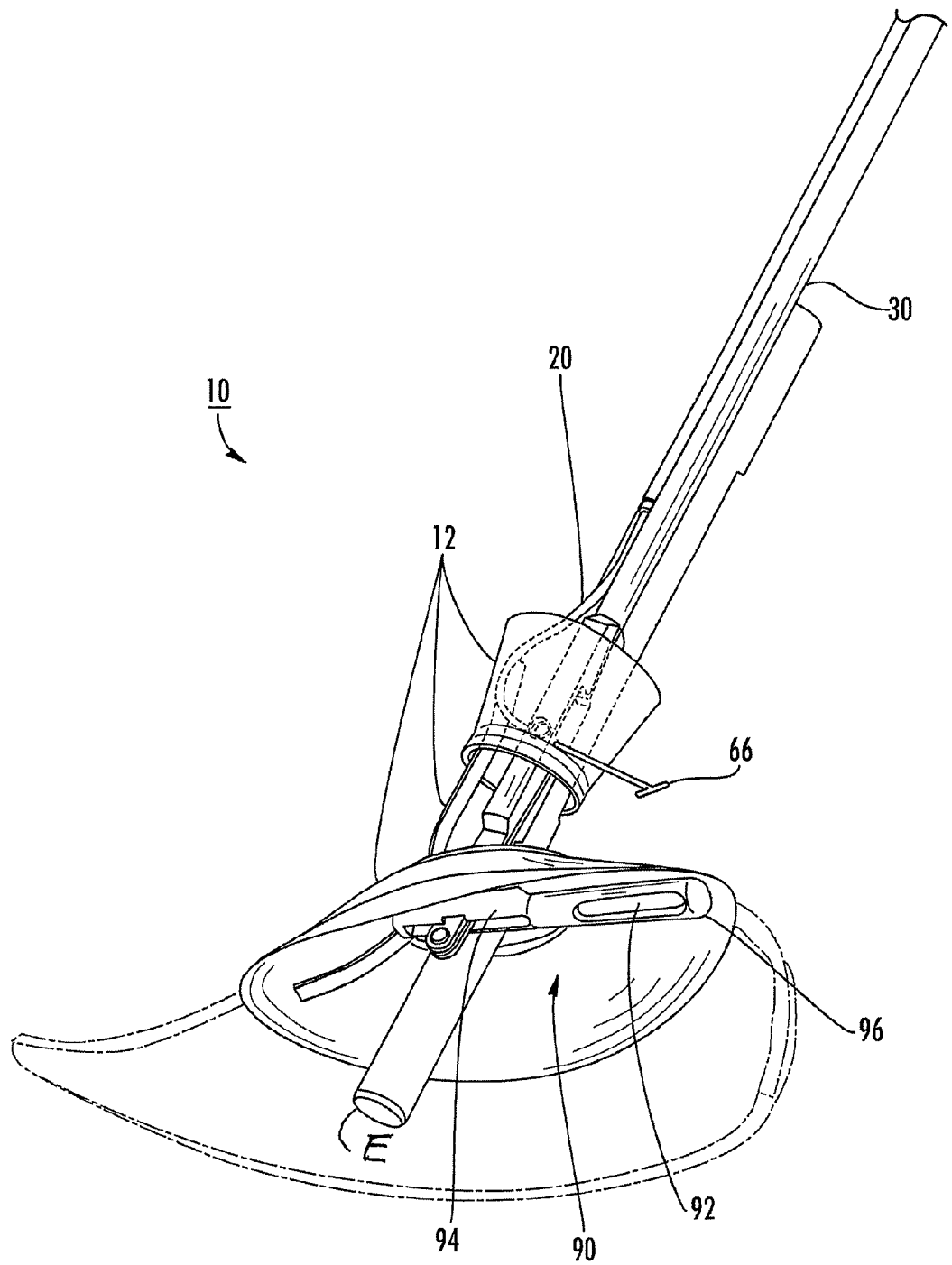
FIG. 1 is a perspective view of a medical device fixation tool juxtaposed with a medical device.
Figure 2:
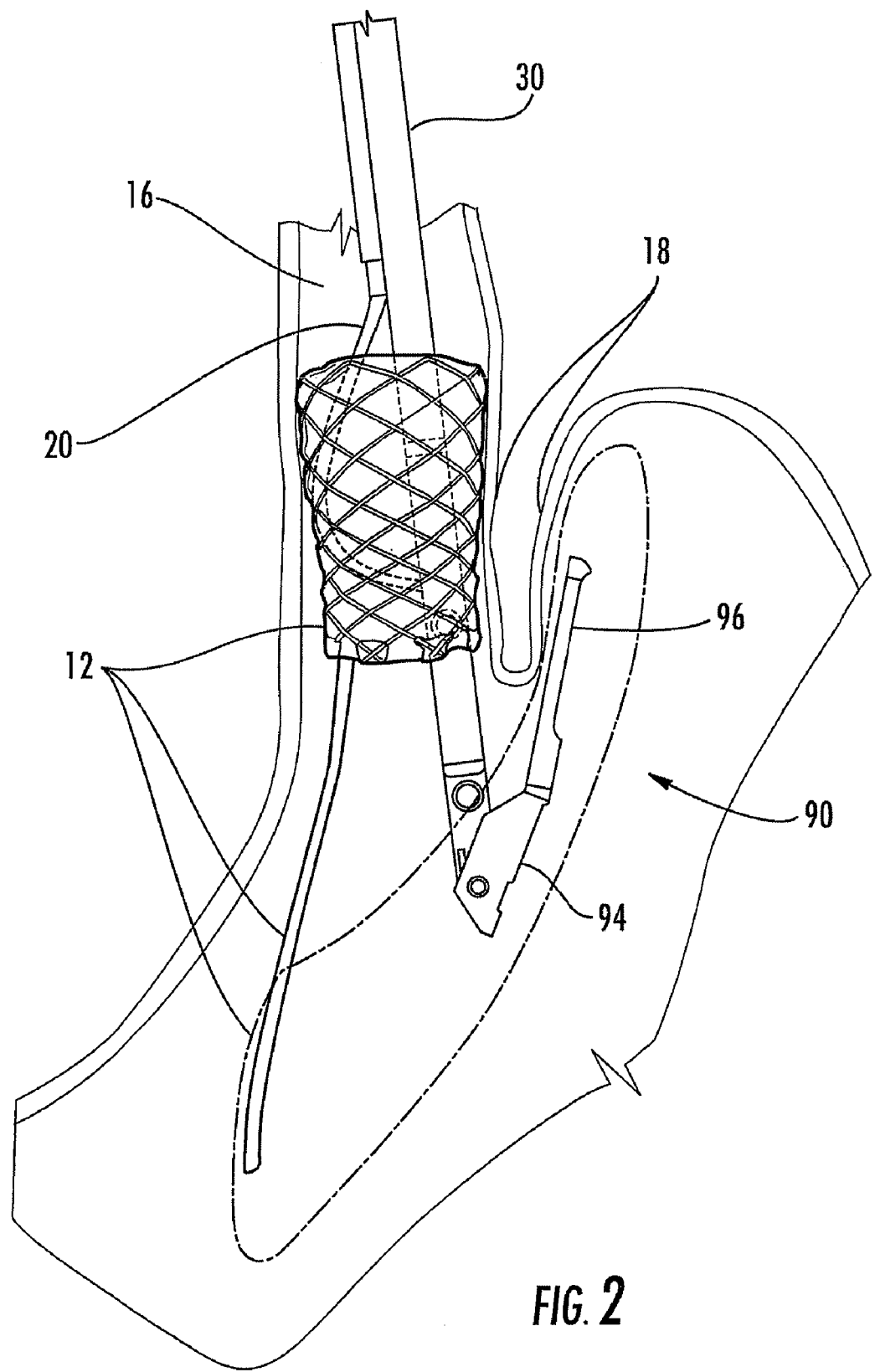
FIG. 2 is a side elevation view of a medical device fixation tool and medical device in FIG. 1.

Referring now specifically to the drawings and the illustrative embodiments depicted therein, a medical device fixation tool, such as a tether application apparatus 10 includes a needle driver assembly 18 and a shaft 30 used to position at least a portion of needle driver assembly 18 within a hollow organ or cavity 16 (FIGS. 1 though 15). The tether application apparatus 10 may further include a support 90 to offer resistance to distal movement resulting from forces arising when needle 24 penetrates a material, such as mammalian tissue or a wall of a medical device 12.

Tether application apparatus 10 is adapted to aid installation of a medical device 12, such as a bariatric device of the type disclosed in commonly assigned International Patent Application Publication No. WO 2008/101048 A2 and patent application Ser. Nos. 60/901,457 filed Feb. 14, 2007; 60/921,930, filed Apr. 5, 2007 and 12/539,112 filed Aug. 11, 2009 entitled BARIATRIC DEVICE AND METHOD, the disclosures of which are hereby incorporated herein by reference in their entirety. Shaft 30 may be deployed endoluminally through a natural orifice, such as the esophagus via an overtube. The support 90 is then deployed in a manner described in detail below. Needle driver 18 is actuated to drive needles 24 connected with the tether filament 62 through a first portion of medical device 12, and mammalian tissue, such as the wall of the patient's esophagus, the wall of the patient's stomach at the cardia, and a second portion of a medical device 12. The support 90 is then retracted and the tether application apparatus is withdrawn.

Figure 3:
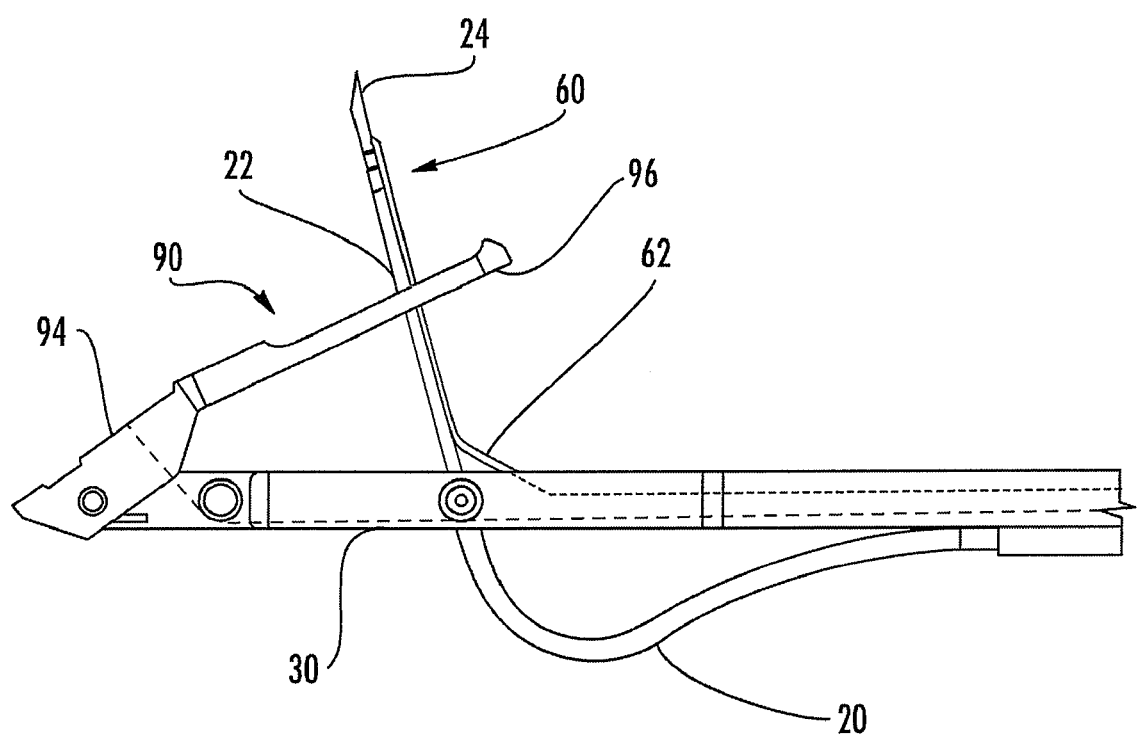
FIG. 3 is a side elevation of a distal portion of the medical device fixation tool illustrating the relationship between the needles and needle driver and the support.
Figure 4:
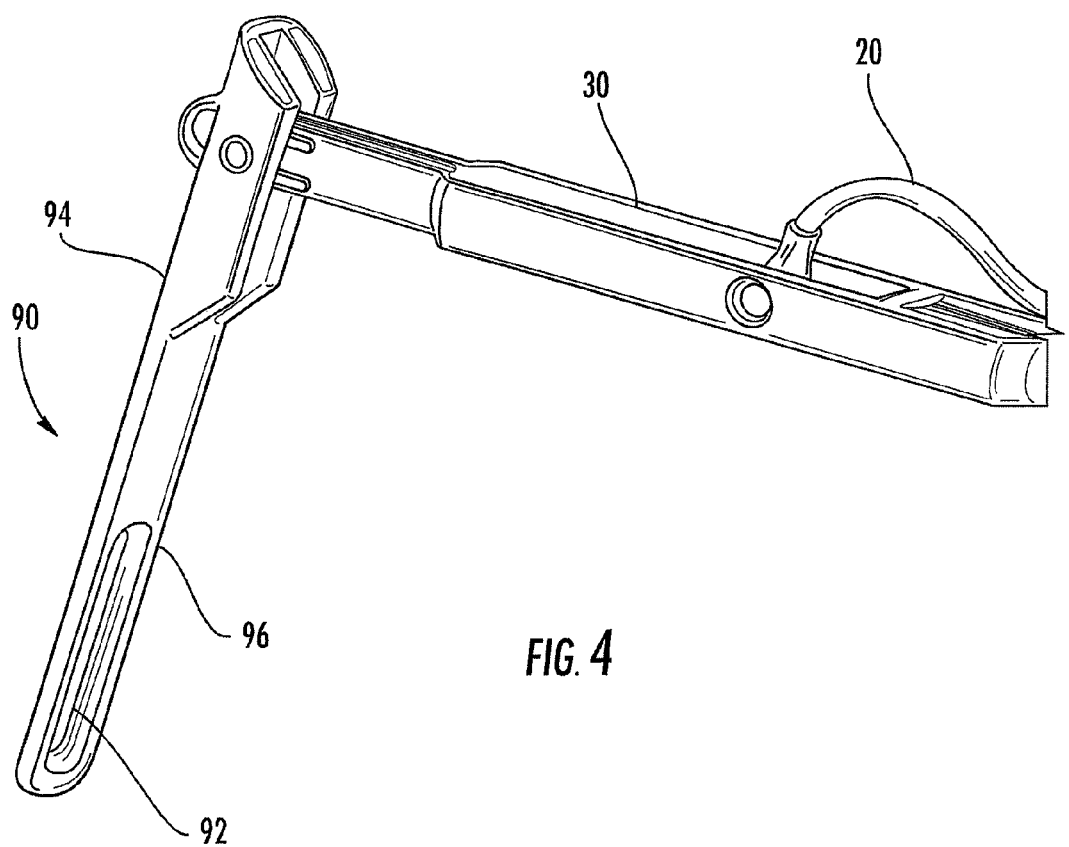
FIG. 4 is a perspective view of the distal portion of the medical device fixation tool in FIG. 3.
Figure 5:
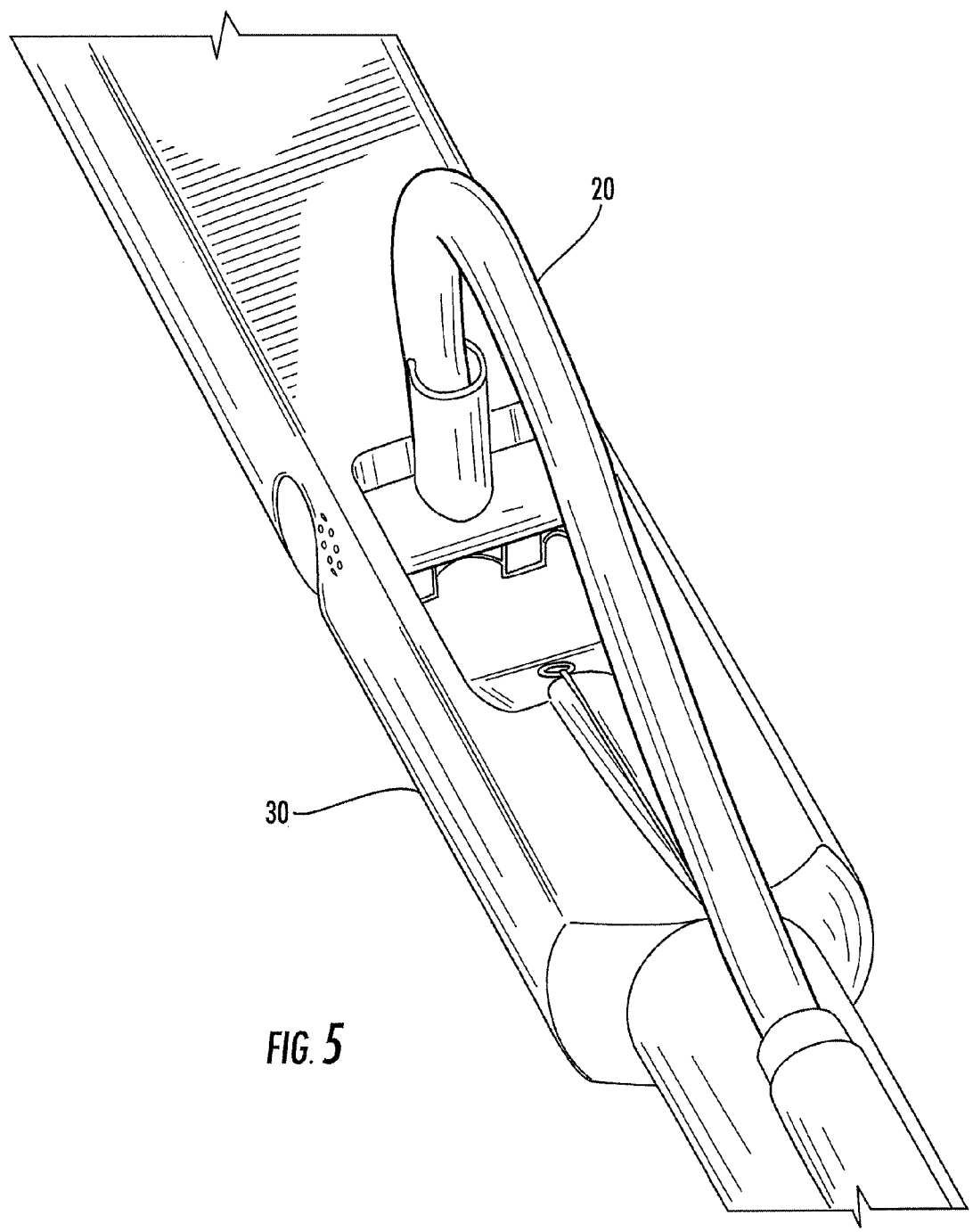
FIG. 5 is an enlarged perspective view of a medical device fixation tool in FIG. 3 illustrating aiming of the needle driver.

Referring now to FIGS. 3 through 5, support 90 is pivotally mounted to a distal end of shaft 30 with a pivot 32. Support 90 is moveable between a use position illustrated in FIG. 3 and a deployment position illustrated in FIG. 6 by a pull wire 34 that is reeved about a pulley 36. A spring (not shown) biases support 90 to the extended position in FIG. 6, and pull wire 34 moves support 90 to the position in FIG. 3.

Needle driver 18 may include a needle housing 22, a needle guide 20 that can be aimed, and a needle pusher assembly 26 that is moveable within needle guide 20 to drive the needle. Needle guide 20 includes a tube 21 that moves with respect to housing 22 and a yoke 27 that receives a distal end of tube 21 and pivots with respect to shaft 30. Needle guide 20 is capable of being aimed by the physician from outside the patient. This may be accomplished in the illustrated embodiment by a pivot yoke 27 pivoting with respect to shaft 30, as best seen in FIG. 5. Needle pusher assembly 26 slides in tube 21 as tube 21 is paid out through pusher housing 22 and receives a needle 24. Connector material 60, such as needle 24 operatively connected with a tether 62 is delivered by pusher assembly 26. Needle pusher assembly 26 is capable of applying a sufficient force on needle 24 to penetrate through one or more walls of medical device 12. Tether 62 extends through a cavity in shaft 30 to the proximal end of shaft 30. Alternatively, tether 62 can run along side shaft 30 external of the patient.

Yoke 27 allows needle tube 21 to be adjusted to lie substantially along the face of shaft 30 in a deployment position, thereby easing deployment of the medical device fixation tool in a hollow organ or cavity 16. Needle tube 21 may also be adjusted to displace from such deployment position to a use position by distally displacing a greater length of needle tube 21 out of pusher housing 22, one illustration of which appears in FIG. 3. In this use position, needle guide 20 may be further adjusted to allow needle pusher 26 to substantially align needle 24 with a desired location on medical device 12 when support 90 is in a use position. Accordingly, pusher assembly 26 may deliver connector material 60 through material lying between support 90 and shaft 30, such as mammalian tissue and a wall of medical device 12.

Referring now to FIG. 4, support 90 may have a first portion 94 and a second portion 96. The first portion 94 includes pivot 32 attaching to shaft 30, allowing support 90 to rotate about the pivot into a range of positions with respect to shaft 30. For endoluminal deployment of the medical device fixation tool, the support 90 may be pivoted distally into substantial alignment with the shaft (as illustrated in FIG. 6). Alternatively, support 90 may be pivoted proximally into substantial alignment with the shaft for deployment. Second portion 96 may further include a void 92, which may be an aperture, hole, divot, or other void suitable for receiving needle 24 with the rest of second portion 96 surrounding void 92 supporting a portion of medical device 12. In an alternative embodiment (not shown), support 90 may have a surface that is penetrable by needle(s) 24. Thus, as a needle passes through the cardiac member, it also penetrates the proximal surface of support 90 to allow the needle to fully pass through pierced material.

Operation of medical device fixation tool 10 can be understood by reference to FIGS. 6 through 13. Referring now to FIG. 6, medical device fixation tool 10 is shown in a deployment position capable of endoluminal deployment in a hollow organ or cavity 16. Support 90 is pivoted distally into substantial alignment with shaft 30, and needle guide 20 is adjusted to lie substantially along the face of shaft 30. Needle pusher assembly 26 and needle 24 (not shown in FIG. 6) are in the deployment position. A needle control handle 40 is shown with a grasping handle 42, a needle guide 46 in the deployment position, and a two-part needle deployment actuator 48 in the retracted position. A support control handle 50 includes a support actuator 56 in the retracted position. The proximal end of tether 62 is shown protruding from the proximal terminus of shaft 30. After a physician has satisfactorily positioned shaft 30, such as through an overtube positioned in the hollow organ or cavity 16, deployment of the medical device fixation tool may begin. Deployment may be visualized fluoroscopically or by an endoscope E that can be inserted in the same overtube as shaft 30, as best seen in FIG. 1.

Referring now to FIG. 7, support 90 is pivoted into a partially deployed position by rotating support actuator 56 on support control handle 50. The physician may use grasping handle 52 to aid in manipulation of support control handle 50. Actuator 56 may be connected to a lead screw (not shown) that converts rotational motion to linear motion of pull wire 34, which is connected between the lead screw and support 90. It will, however, be apparent to the skilled artisan that other ways to accomplish the actuation of support 90 are possible.

Figure 8:
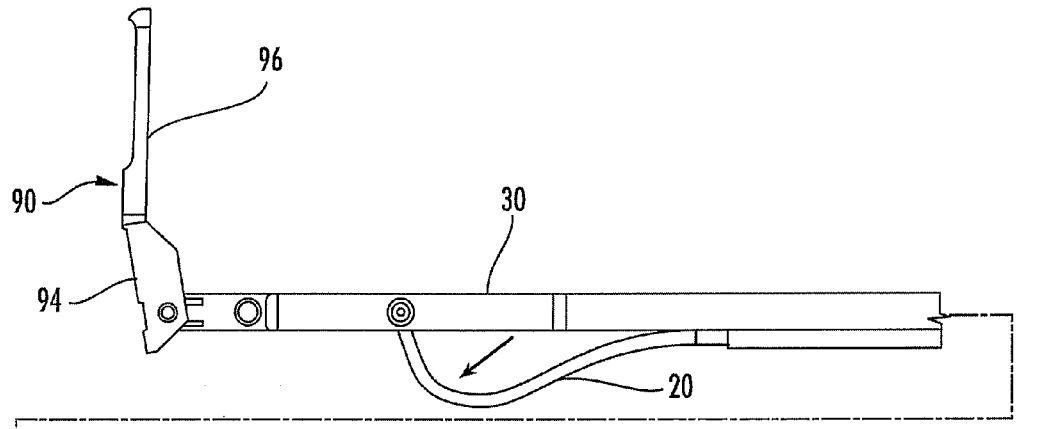
FIG. 8 is the same view as FIG. 7 with the needle guide being aimed.

Referring now to FIG. 8, needle guide 20 is moved to a use position by elongating needle tube 21 from pusher housing 22. This may be accomplished by sliding needle guide actuator 48 on needle control handle 40. Needle guide 20 is adjusted to be substantially aligned with the desired path of needle pusher assembly 26 and, hence, to aim delivery of needle 24.

Figure 9:
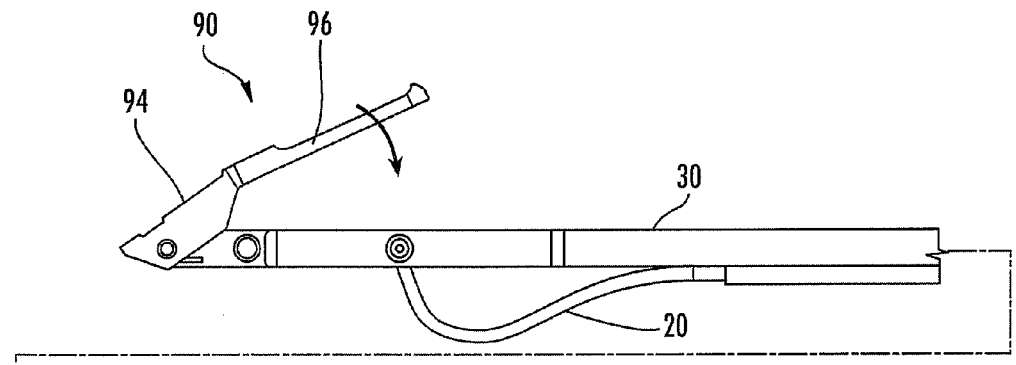
FIG. 9 is the same view as FIG. 8 with the support fully deployed in a use position.

Referring now to FIG. 9, support 90 is pivoted into a use position by further rotating actuator 56 on control handle 50, as described above. The use position is the position where second portion 96 is able to support any portion of medical device 12 to be transversed by needle 24 against distal movement in the direction of needle travel. In this position, needle 24 is substantially aligned with central void 92, so that needle 24 may pass into or through central void 92.

Figure 14:
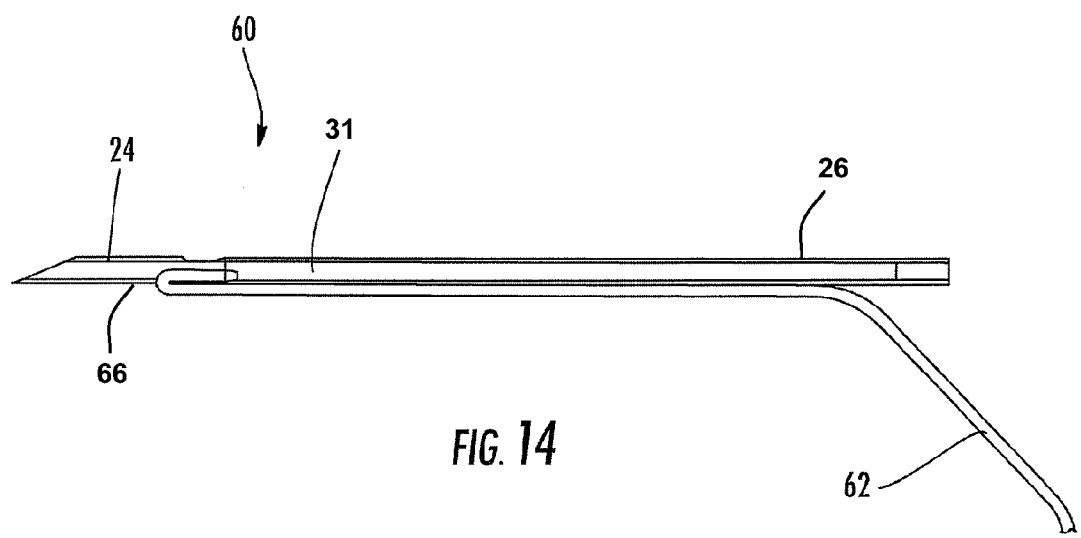
FIG. 14 is a side elevation of an embodiment of a tether clamp device connected to a tether.

Referring now to FIG. 10, needle pusher assembly 26 is deployed by distal sliding of second actuator 48 on needle control handle 40. Needle pusher assembly 26 is configured to support needle 24 in a manner that provides a smooth transition between the outer surface of needle deployment tube 29 and needle 24 (FIG. 14). Needle 24 may, in turn, be connected to a distal portion of tether 62, which may travel along shaft 30 to a proximal portion in the vicinity of needle control handle 50, thereby allowing the operator to access tether 62 after it is connected. Needle deployment filament 31 is positioned within deployment tube 29 (FIG. 14) and is also movable by needle deployment actuator 48. In particular, a first portion 48a of needle deployment actuator 48 moves needle deployment tube 29 and a second portion 48b of needle deployment actuator 48 moves needle deployment filament 31. When both portions 48a and 48b are moved together, as illustrated in FIG. 10, needle deployment tube 29 and needle deployment filament 31 move distally together. The physician may use grasping handle 42 to aid in manipulation of needle deployment actuator 48. Although linear actuation with needle deployment actuator 48 is disclosed herein, it will be apparent to the skilled artisan that other ways to accomplish the actuation of needle deployment tube 29 are possible.

Figure 12:
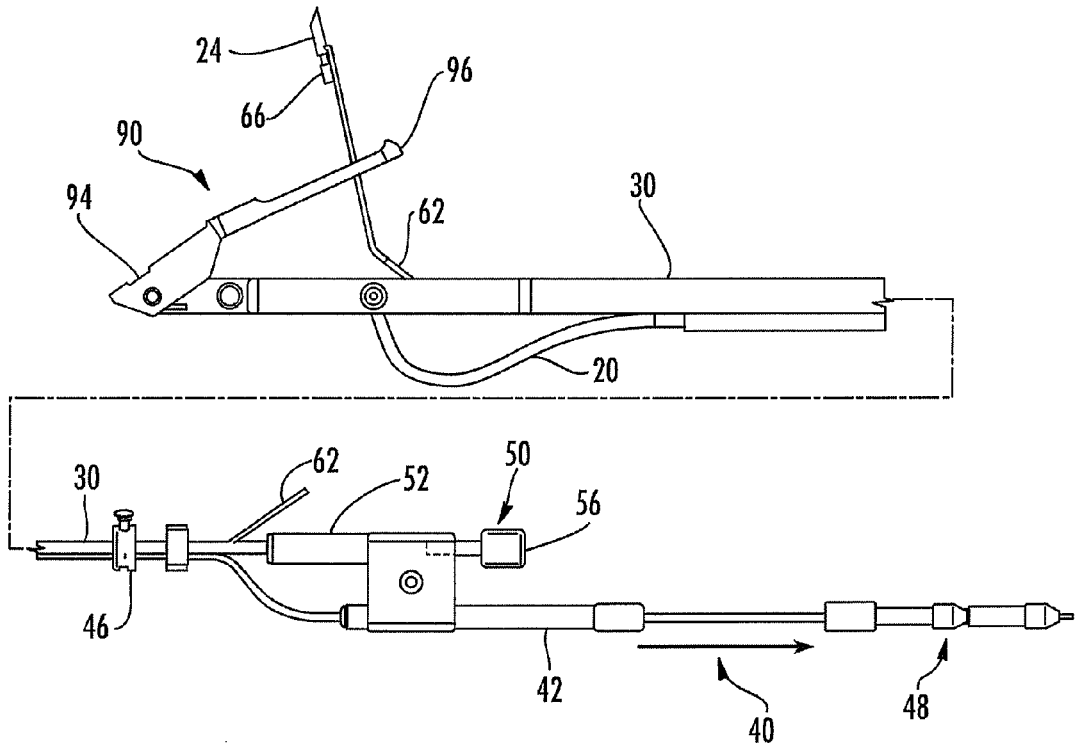
FIG. 12 is the same view as FIG. 11 with the needle guide in a partially retracted position and the needle remaining deployed.

Referring now to FIG. 11, with needle deployment tube 29 and needle deployment filament 31 in use positions, needle 24 is deployed by being dislodged from needle deployment tube 29 by proximal sliding of portion 48b of second actuator 48 on needle control handle 40 relative to portion 48a. This causes needle control filament 31 to move relative to needle deployment tube 29, thus freeing needle 24 from the needle deployment tube. In the illustrated embodiment, this is accomplished by needle control filament 31 retracting proximally with respect to needle deployment tube 29. However, medical device fixation tool 10 could be configured for needle control filament 31 to extend relative to needle deployment tube 29 to deploy the needle. As seen in FIG. 12, movement of actuator portion 48a will retract needle deployment tube 29 such that needle pusher assembly 26 is now fully retracted reversing the motion shown in FIG. 10 and described above.

Figure 13:
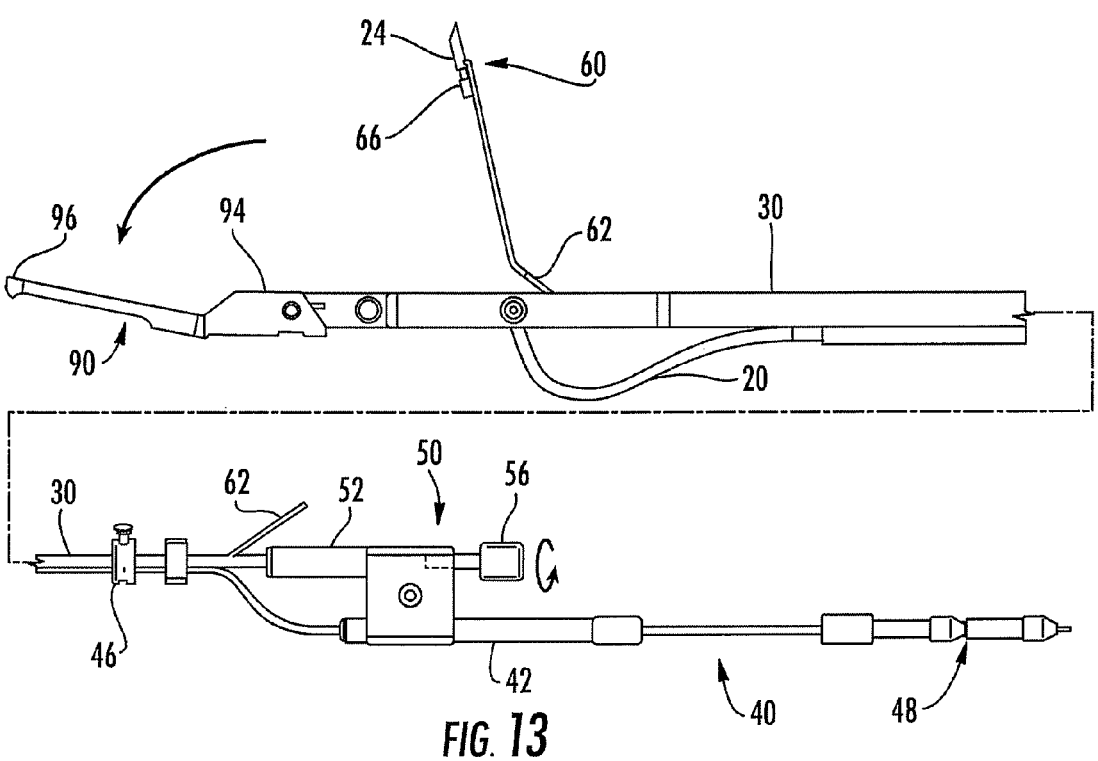
FIG. 13 is the same view as FIG. 12 with the support distally retracted.

Referring now to FIG. 13, support 90 can be pivoted to the deployment position substantially aligned with shaft 30 in preparation for removal of the medical device fixation tool from hollow organ or cavity 16. Such pivoting is accomplished by rotation of actuator 56 on support control handle 50, in reverse of actions shown in FIGS. 7 and 9 and described above. Central void 92 in second portion 96 of support 90 clears connector material 60 and needle 24, if it is present. Needle guide 20 may then be adjusted to a deployment position using first actuator 46 on needle control handle 40, and the medical device fixation tool can be removed from hollow organ or cavity 16.

Referring now to FIG. 14, one embodiment of connector material 60 is illustrated. Connector material 60 includes needle 24 that is integral with a "T" clamp device 66, so that after deployment the tip of needle 24 forms a portion of the top of the "T". Tether 62 forms the trunk of the "T" and is connected to the needle 24, such as by crimping the needle. Thus, after needle pusher assembly 26 has driven needle 24 through mammalian tissue, medical device 12, or other material, needle 24 will rotate and hold tether 62 against a distal surface of such material.

Figure 15:
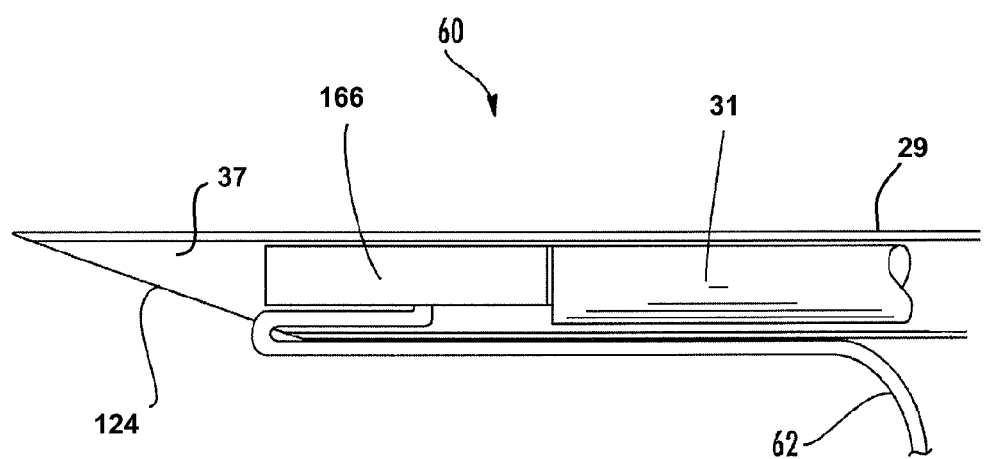
FIG. 15 is an enlarged elevation of an alternative embodiment of the tether clamp device.

Referring now to FIG. 15, another embodiment is shown of the connector material. In this embodiment, a needle 124 is connected to needle deployment tube 29, so that needle 124 is manipulable by manipulating needle deployment tube 29 and will withdraw after deployment. A "T" clamp device 166 is contained within a hollow cavity 37 of needle 124 in alignment with needle deployment filament 31. When ready for deployment, needle deployment filament 31 ejects "T" clamp device 166 from hollow cavity 37, enabling "T" clamp device 166 to unfold and anchor against a distal surface of pierced material. Needle 124 and deployment tube 29 may be commonly made from a laterally flexible yet longitudinally non-compressible material, such as a Nitinol tube that is ground to a beveled point. Tether 62 forms the trunk of the "T" and passes through pierced material, enabling connections or other manipulations from the proximal portion of tether 62. Alternatively, tether 62 may pass through the barrel of deployment tube 29 to a proximal terminal portion thereof.

The embodiment illustrated in FIG. 15 allows the physician to retract needle 124 even after it has transversed the portion of the medical device, such as the cardiac portion in the case of a bariatric device. In this manner, should the physician not be pleased with the location of the penetration, the physician can retract the needle and reposition it. Once the physician is satisfied with the location, the T-clamp can then be deployed.

Figure 16:
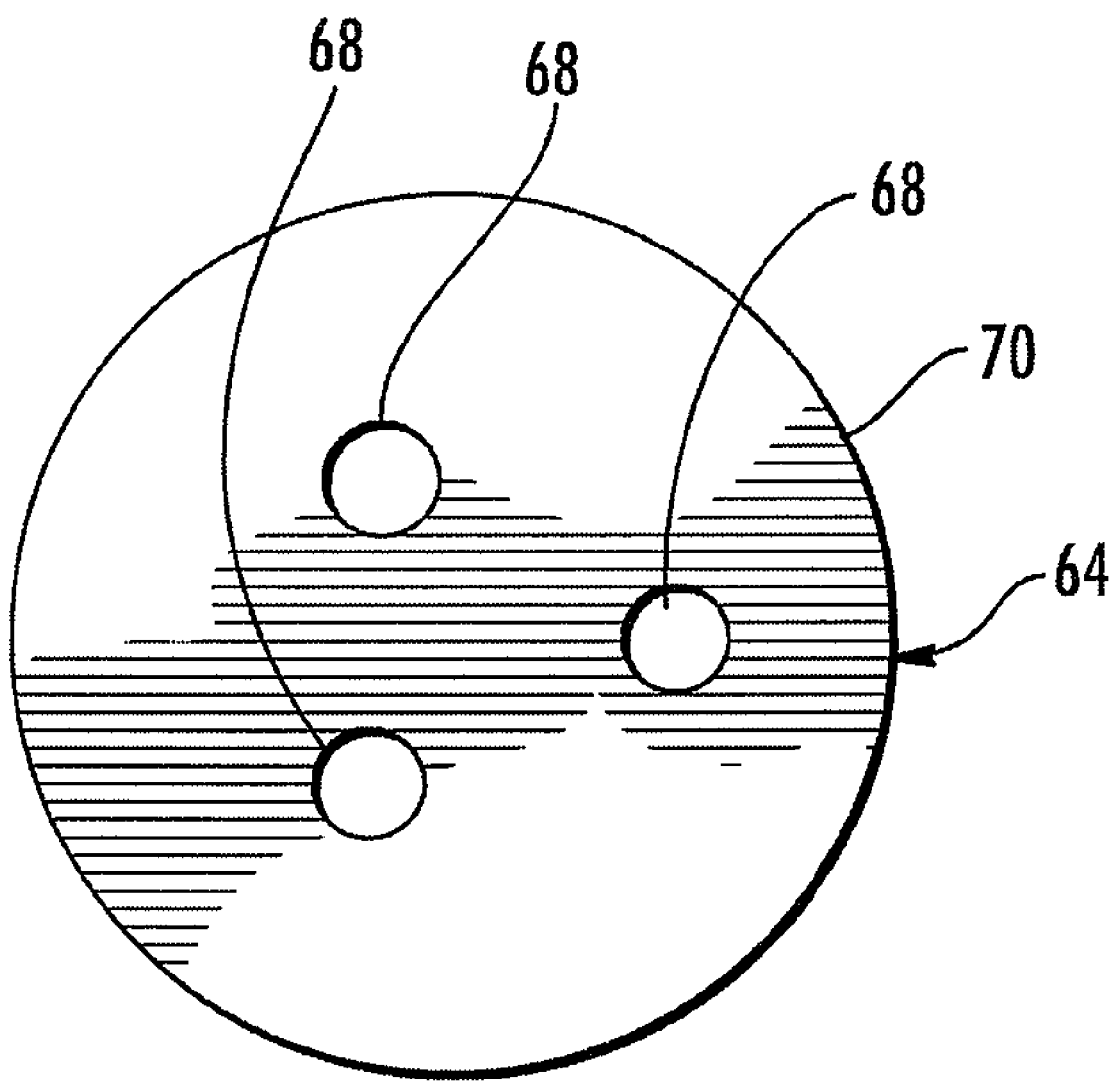
FIG. 16 is an elevation of a tether clamp.
Figure 17:
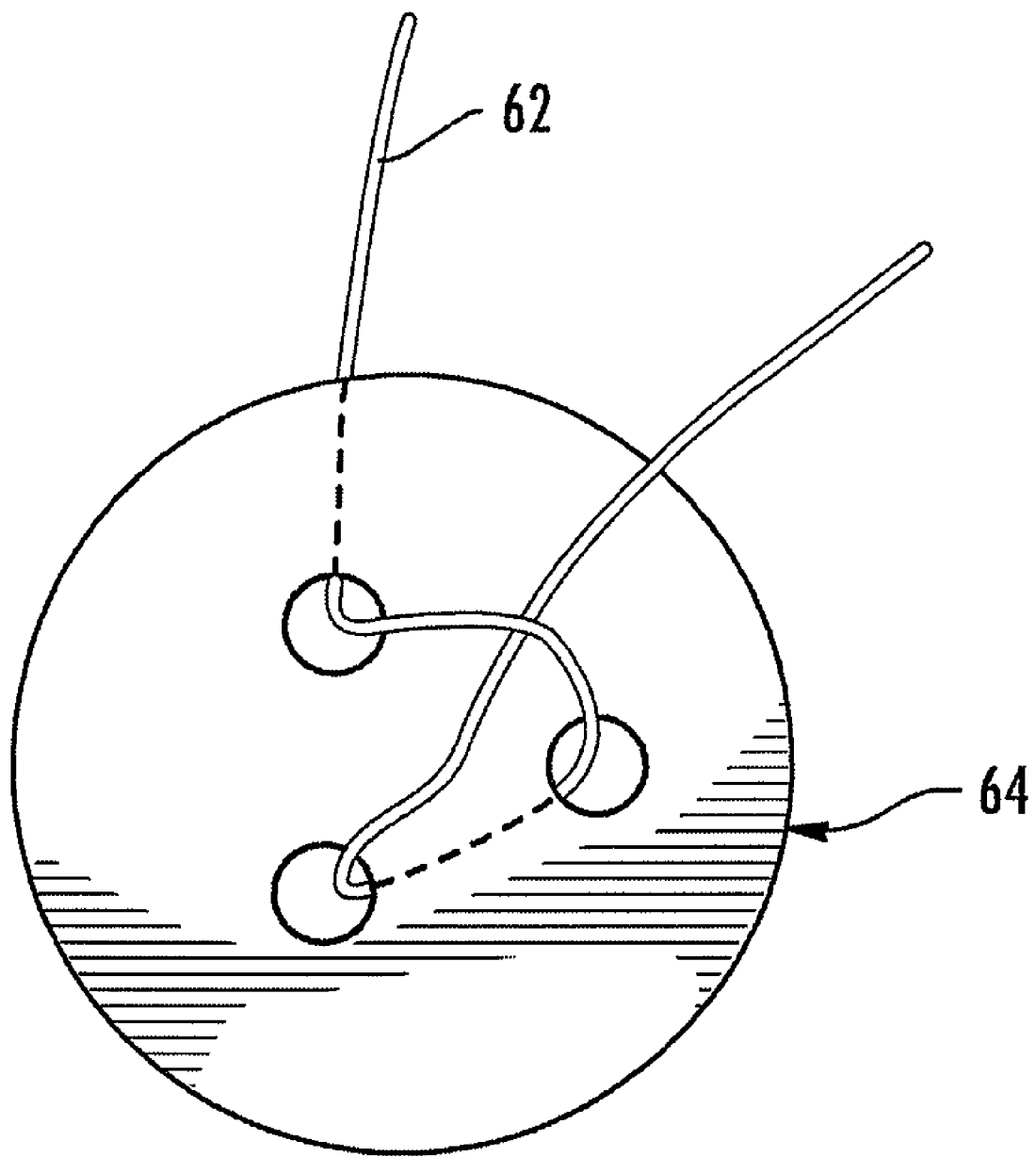
FIG. 17 is the same view as FIG. 16 illustrated with a tether.

Referring now to FIGS. 16 and 17, the proximal end of tether 62 may be clamped using a clamp device in the form of a button 64 in the form of a disk 70 containing a plurality, such as three (3), of through-openings 68. Disk 70 may be made of a suitable material, such as polycarbonate, or the like. As illustrated in FIG. 17, button 64 is attached to the proximal end of the tether 62 by passing an end of the tether under a loop formed by the tether thereby forming a one-way clamp that operates similarly to a slipknot. This allows the tether clamp to be propelled along the tether from external the patient to a position engaging the proximal surface of mammalian tissue, medical device 12, or other material and snugged up to a desired tension of the tether 62, using a conventional knot pusher, or the like. Although the tether clamp can move relatively freely in one direction for deployment, it resists movement in the other direction, thereby firmly engaging the proximal surface of mammalian tissue, medical device 12, or other material. A roughened portion 72 of the surface 74 of disk 70 may be provided to help lock the tether to resist movement of button 64. Also, an elongated extension of surface 74 (not shown) may be provided on either side of opening 68 to trap or pinch a portion of the tether. For additional stability, the physician may choose to tie a slipknot to the ends, if more than one tether is used, and slide the slipknot against the button 64 within the esophageal member using a knot pusher.

In an alternative embodiment, pivot 32 can be made adjustable along shaft 30. This allows the amount of tissue captured between support 90 and shaft 30 to be varied. Also, although the fixation tool is illustrated as a unitary assembly, a separate needle pusher, or needle driver, may be provided. This would allow the shaft and support, including associated actuator, to be provided as a separate support unit that can be separately positioned in the hollow organ or cavity. The support unit may include a plurality of openings that are adapted to receive the separate needle pusher. The openings are oriented to provide the physician the ability to aim the needle driver differently based upon which opening is engaged by the needle driver. The needle driver may be an integral unit made, by way of example, from hypodermic tubing which is commercially available. The separate needle driver may be deployed in a working channel of an endoscope.

Figure 18:
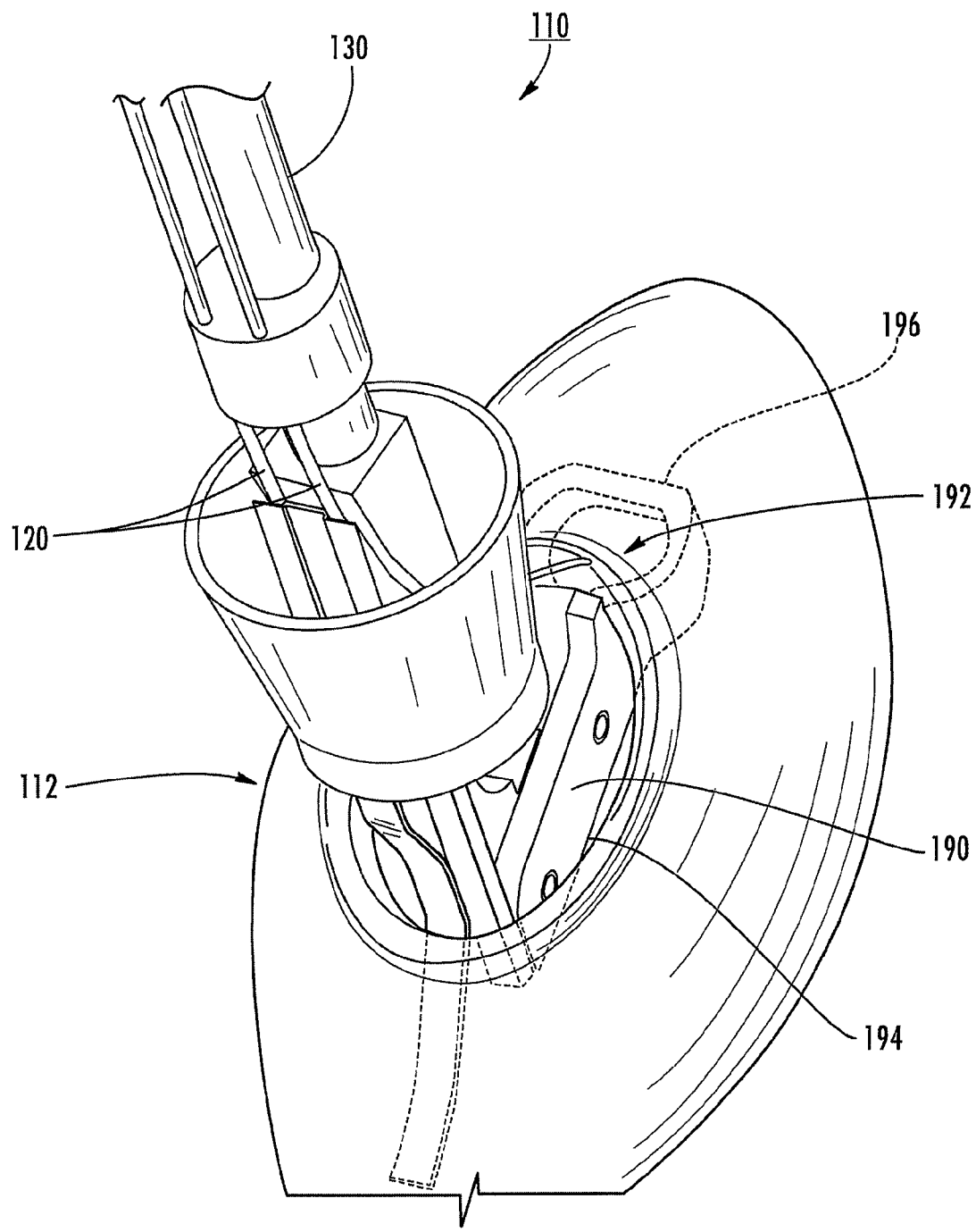
FIG. 18 is a perspective view of an alternative embodiment of a medical device fixation tool juxtaposed with a medical device.
Figure 20:
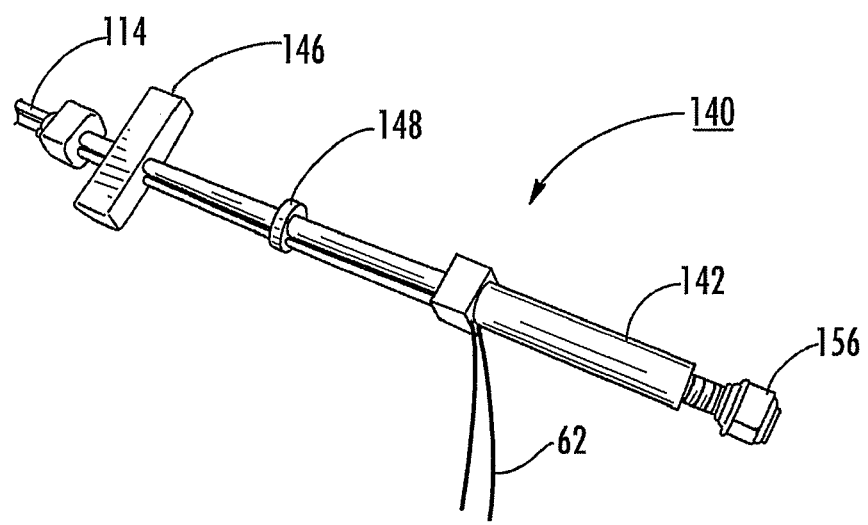

Referring now to FIGS. 18 and 20, an alternative embodiment of tether application apparatus 110 may include a shaft 130 that is of a cross-sectional configuration and length that is adapted to extend through an overtube transorally to a patient's stomach. Tether application apparatus 110 may include an actuator 140 proximal of shaft 130. Actuator 140 remains external the patient during a medical procedure, such as a bariatric device deployment procedure. Shaft 130 may be covered by a sheath 114. Actuator 140 may include a grasping handle 142, a support positioning actuator 156, a needle guide actuator 146, and a needle firing actuator 148, although certain of these actuators may be combined for ease of use.

Figure 19:
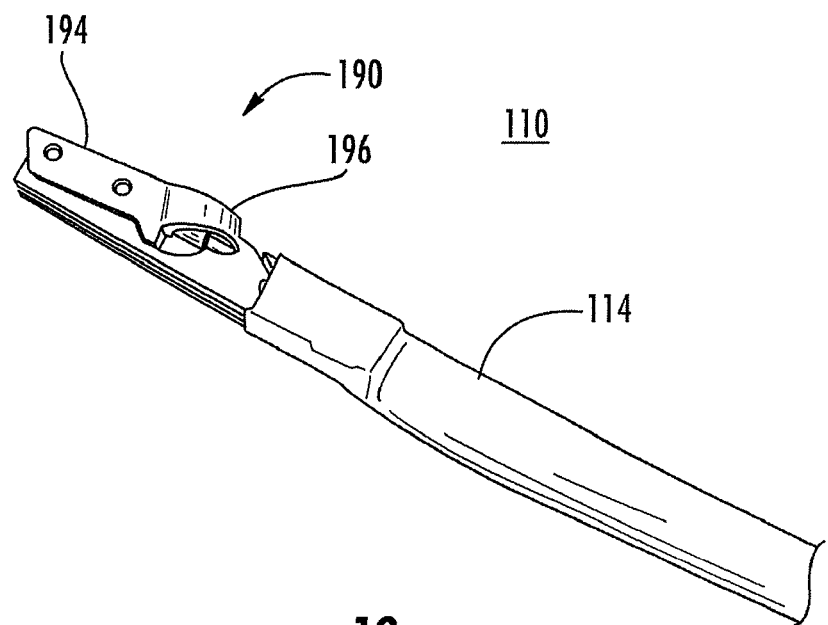
FIGS. 19 and 20 are perspective views of a medical device fixation tool and actuator in FIG. 18 in a deployment position.
Figure 21:
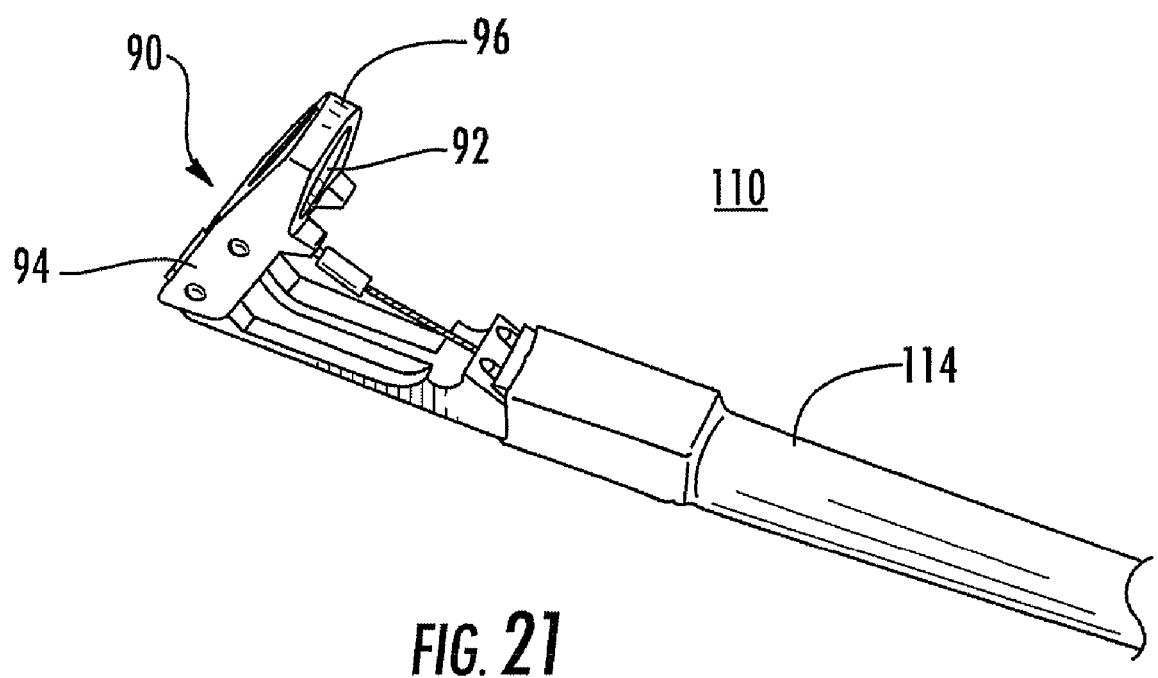
FIG. 21 is the same view as FIG. 19 with the support in the use position.

FIGS. 19 and 20 illustrate tether application apparatus 110 with support 190 in a deployment position in which it is capable of traversing a patient's esophagus through an overtube. Once support 190 is positioned within the stomach, operation of support actuator 156 causes support 190 to pivot to a use position, as illustrated in FIG. 21. In the illustrative embodiment, this is accomplished by rotating cardia member support actuator 156. However, other mechanical actuating techniques may be used. Once the support is deployed, proximal movement of grasping handle 142 will cause support 190 to provide distal support to the cardia.

Figure 22:
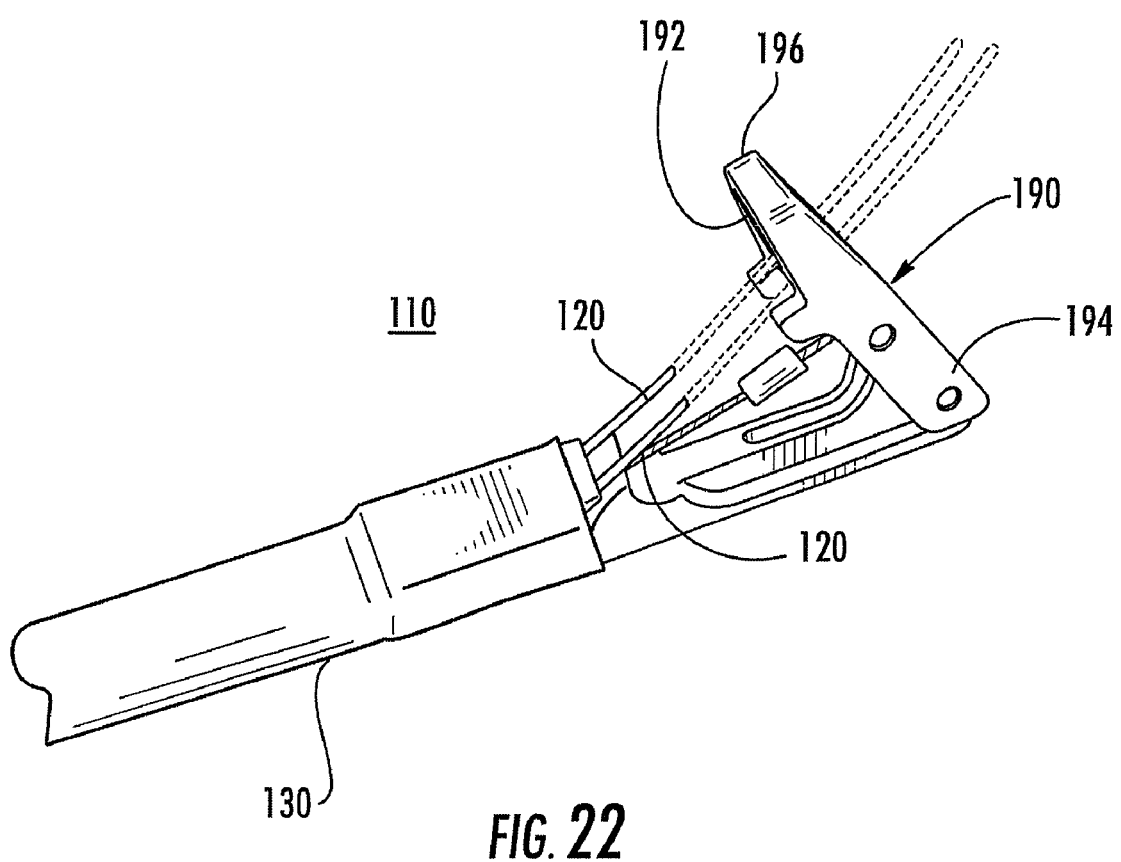
FIG. 22 is a similar view to FIG. 19 illustrating the needle driver being deployed.
Figure 23:
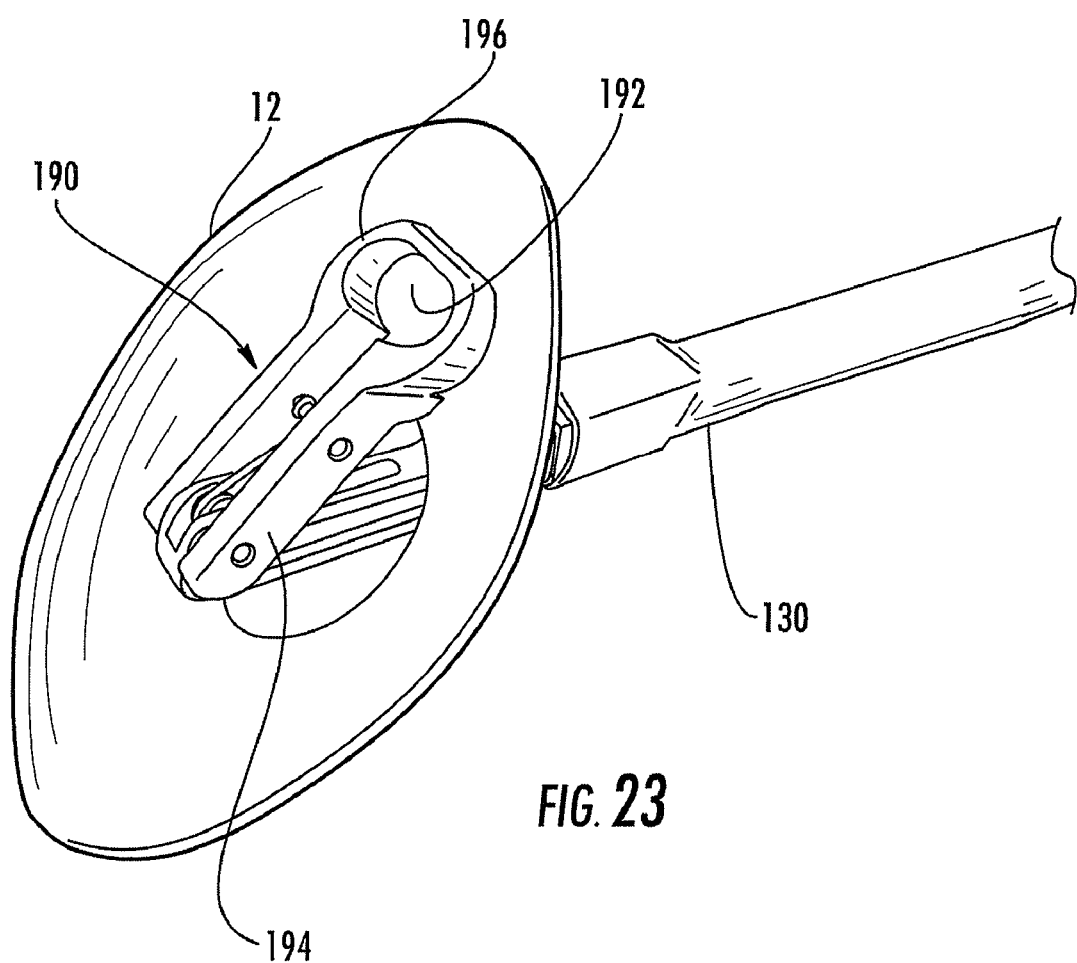
FIG. 23 is a perspective view illustrating the support juxtaposed with a cardiac member body.

Referring now to FIGS. 22 and 23, once the tether application apparatus 110 is oriented properly, a physician operates the needle guide actuator 146 in order to distally move needle guides 120. If a bariatric device 112 is previously deployed, the physician concurrently aligns the needle guides with the desired position on the esophageal member of such device, which may be marked on the inner wall of the esophageal member in order to assist the physician. In the illustrated embodiment, needle guide actuator 146 is shown as a slide actuator, but other forms of actuator may be utilized.

Once the support 190 is properly supporting the cardia, and the cardiac member if it is present, and the needle guides 120 are properly positioned, a physician operates needle firing actuator 148. This causes needle(s) 124 at the distal portion of the tether(s) to move distally into registration with support 190. This assists deployment of the tether(s) without imparting a significant torque, or rotational movement, between an esophageal member and a cardiac member. In the illustrative embodiment, support 190 includes a first portion 194 and second portion 196. First portion 194 includes a pivot attaching to shaft 130, allowing support 190 to rotate about the pivot into a range of positions with respect to shaft 130. Second portion 196 may further include a void 192, which may be an aperture, hole, divot, or other void suitable for receiving needle 124 or needle pusher 120 while preventing material from passing into void 192. In an alternative embodiment (not shown), support 190 may have a surface that is penetrable by needle(s) 124. Thus, as the needles pass through the cardiac member, they also penetrate the proximal surface of support 190 to allow the needles to fully pass through the cardiac member.

Figure 24:
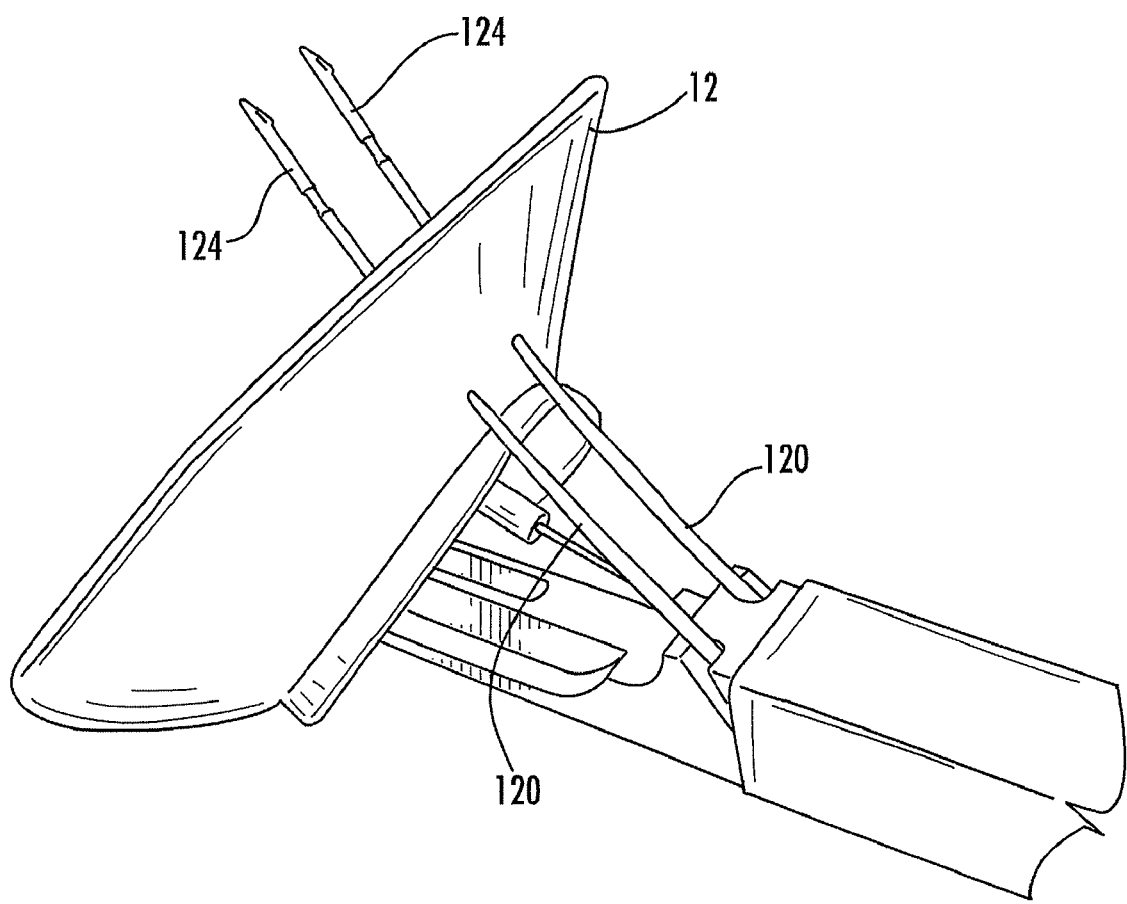
FIG. 24 illustrates tether needles penetrating a cardiac member body.
Figure 25:
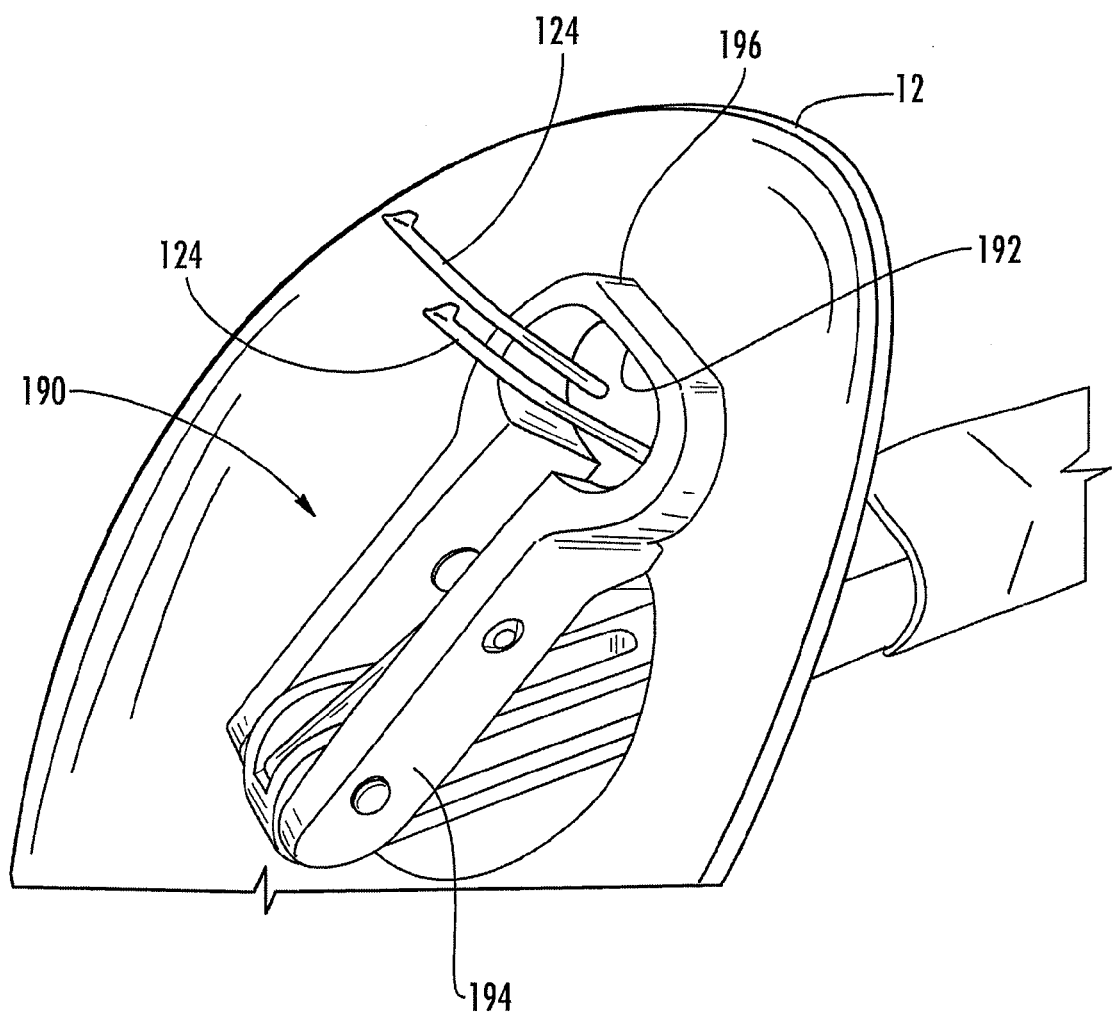
FIG. 25 illustrates accommodation of the tether needles by the support as the needles penetrate a cardiac member.

Referring now to FIGS. 24 and 25, once the needles 124 are properly fired, the operator can remove the tether application apparatus. This may be accomplished by distal movement of the tether application apparatus until support 190 is clear of protruding needles 124. Support actuator 156 can then be operated in order to fold the support 190 against shaft 130 to traverse the esophagus.

Although illustrated for use in deployment of bariatric devices 12 and 112, tether application apparatuses 10 and 110 and/or clamp devices 64 and 66 may find applications for fixation of other medical devices including esophageal stents, anti-reflux devices, nasal gastric tubes, intestinal sleeves, and the like. They may also find other applications including closure of fistulas, tightening of anastomosis, closure of leaks, tightening of a gastric pouch and closure of a gastrotomy. Other applications will be apparent to the skilled artisan.

Figure 26:
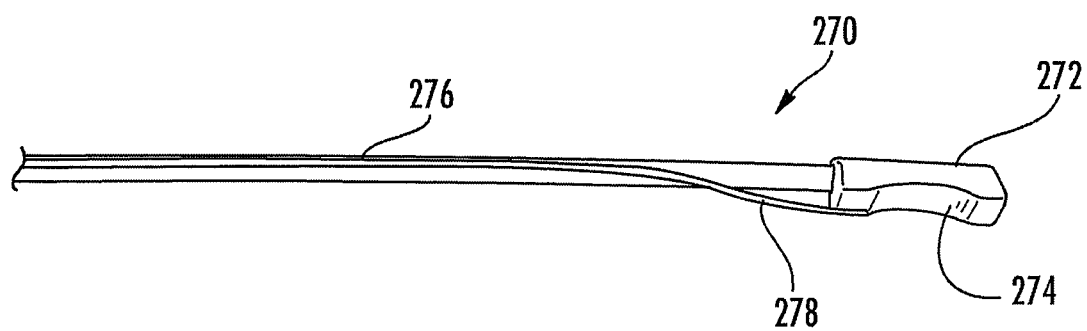
FIG. 26 is a perspective view of another alternative embodiment of a medical device fixation tool.
Figure 27:
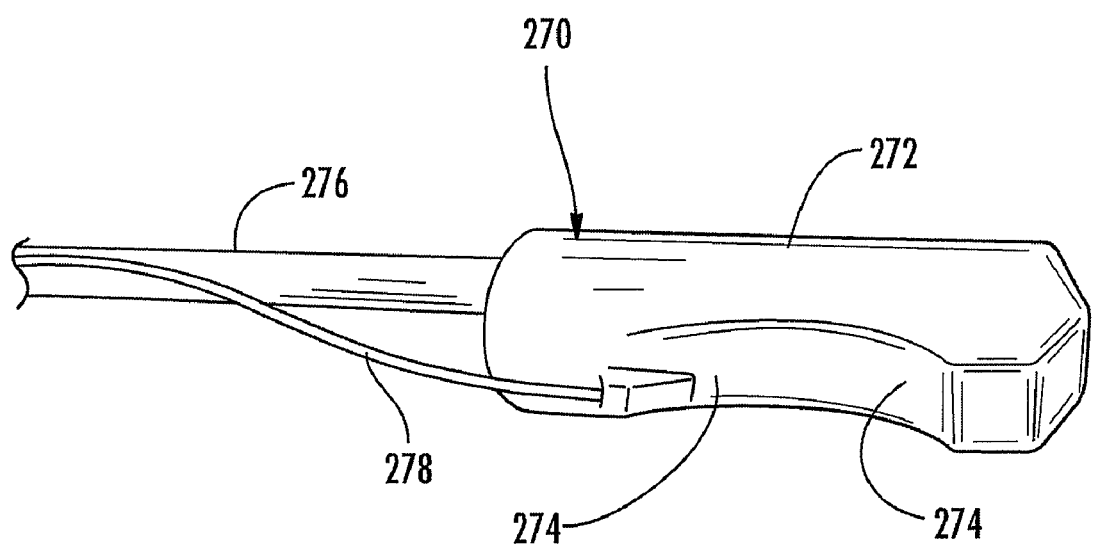
FIG. 27 is an enlarged view of a portion of the medical device fixation tool of FIG. 26.

Referring now to FIGS. 26 and 27, an alternative tether application apparatus 270 includes a head 272 having a window 274 that fires the needle through the tissue. A hollow shaft 276 draws a vacuum at window 274 in order to pull the tissue at the GE junction into the window prior to firing the tether needles. The needle and tether are fired from a tube 278. Shaft 276 may be made flexible to fit the anatomy of the patient, if required.

Figures 28, 29:
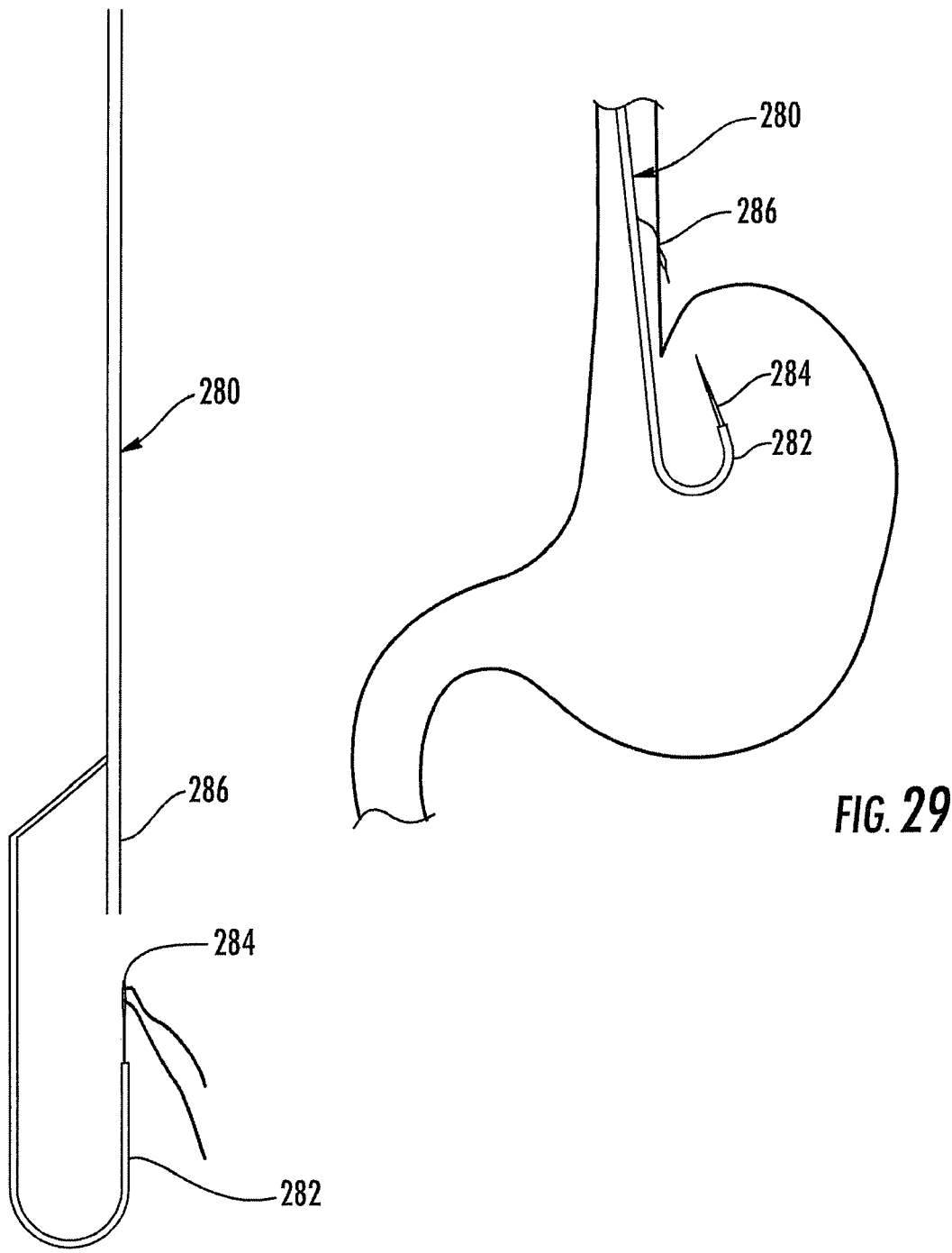
FIG. 28 is a side elevation of another alternative embodiment of a medical device fixation tool.
FIG. 29 is an illustration of the medical device fixation tool of FIG. 28 in use.

Referring now to FIGS. 28 and 29, another alternative tether application apparatus 280 includes a tether tube 282 that passes a needle 284, and attached tether, retroflex from the cardia through the GE junction and into the lower esophagus. It is illustrated as including a sliding needle guide 286 to facilitate passage of the device through the esophagus.

Figure 30:
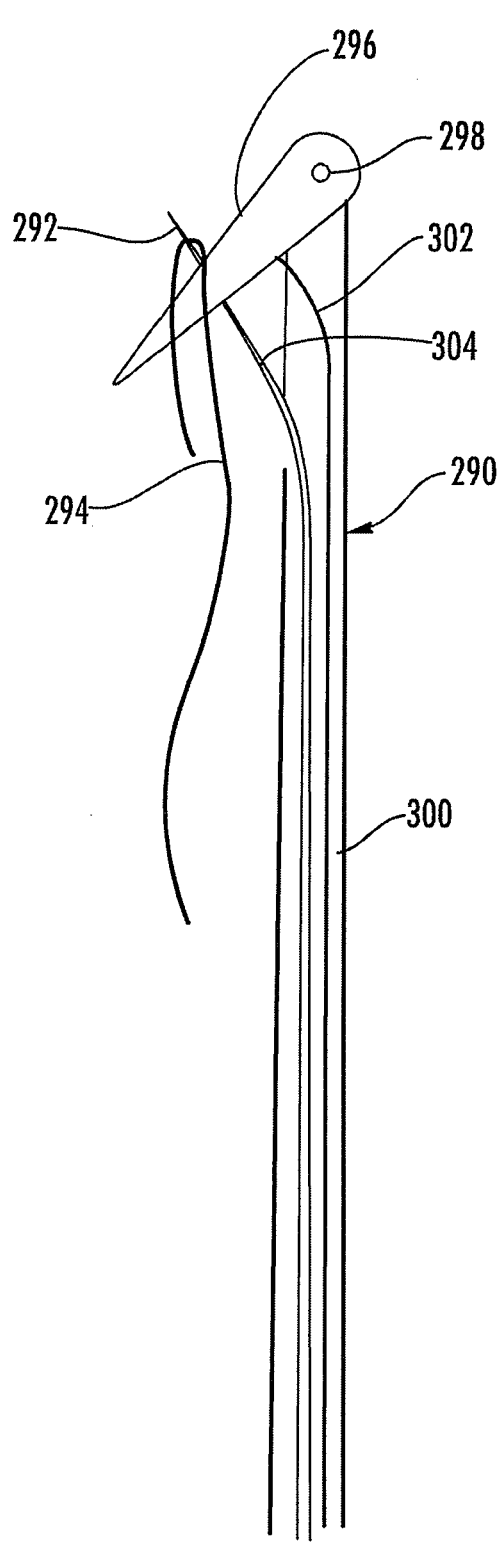
FIG. 30 is a side elevation of another alternative embodiment of a medical device fixation tool.
Figure 31:
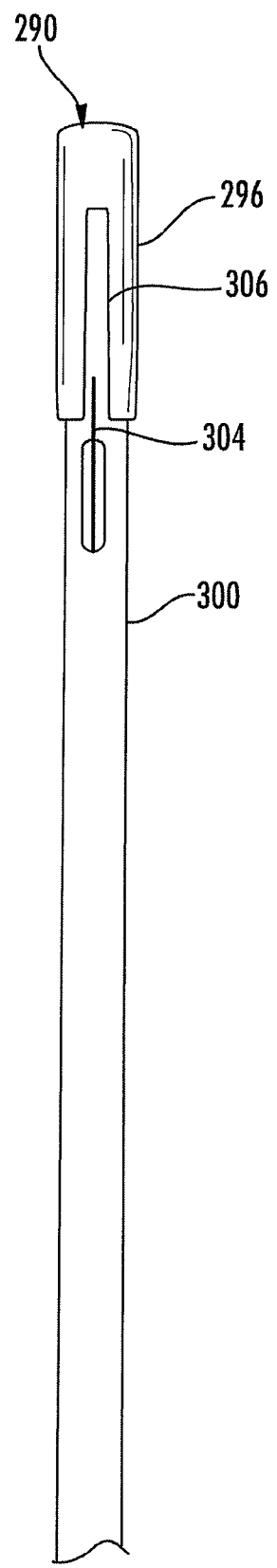
FIG. 31 is another side elevation of the medical device fixation tool of FIG. 30 taken from a different direction.

Referring now to FIGS. 30 and 31, yet another alternative tether application apparatus 290 is used to pass a needle 292 of a tether 294 through the esophagus and into the cardia. A cardia support 296 is pivoted at 298 to a shaft 300. A cable 302 is operated by an actuator (not shown) to pivot the cardia support 296 between a deployment position, for passage through the esophagus, and a use position as illustrated for supporting the cardia. The tether needle is fired through a tube 304. A slot 306 in cardia support 296 facilitates passage of needle 292 while allowing the cardia to be supported.

Figure 32:
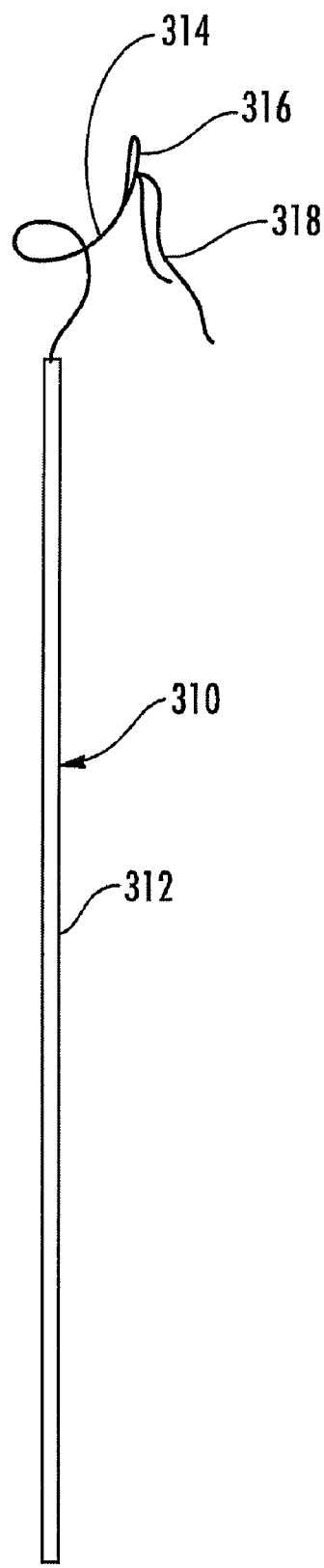
FIG. 32 is a side elevation of another alternative embodiment of a medical device fixation tool.

Referring now to FIG. 32, another alternative tether application apparatus 310 includes a shaft 312 and a spiral formed needle driver 314. Needle driver 314 is used to pass a needle 316 having an attached tether 318 through the lower esophagus and the cardia by twisting shaft 312 and advancing needle driver 314.

Figures 33, 34:
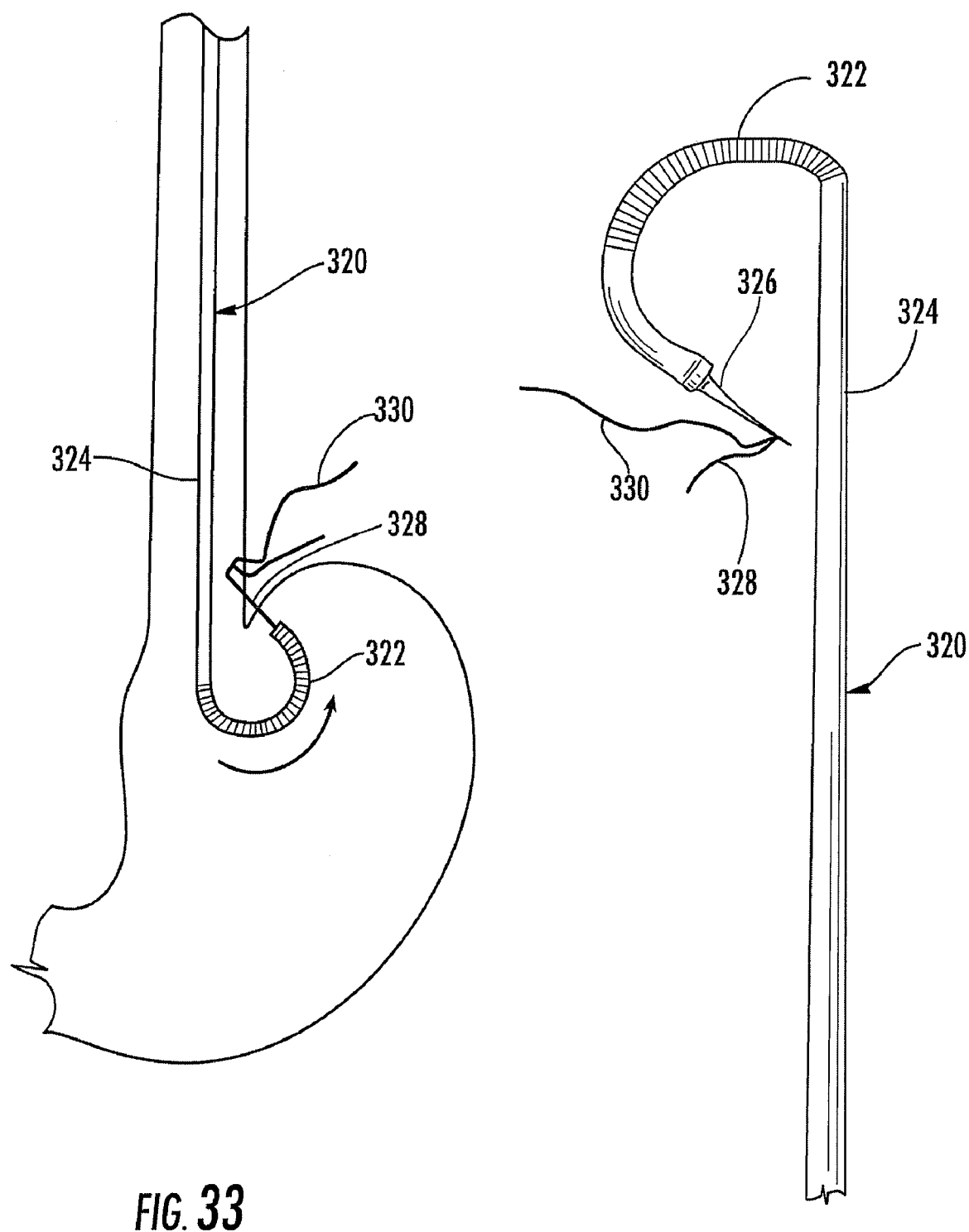
FIG. 33 is a side elevation of another alternative embodiment of a medical device fixation tool in use.
FIG. 34 is an enlarged elevation of the medical device fixation tool of FIG. 33.

Referring now to FIGS. 33 and 34, another alternative tether application apparatus 320 drives the needle in a retroflex manner from the cardia to the GE junction, then into the esophagus. The device includes a flexible neck 322 that is mounted distally on a shaft 324 and supports a needle driver 326. Neck 322 can be straightened for insertion of the device through the patient's esophagus and formed to the shape illustrated in FIG. 34 by the operation of an actuator (not shown). Needle driver 326 drives a needle 328 with attached tether 330 through the cardia, past the GE junction and through the esophageal wall.

Figure 35:
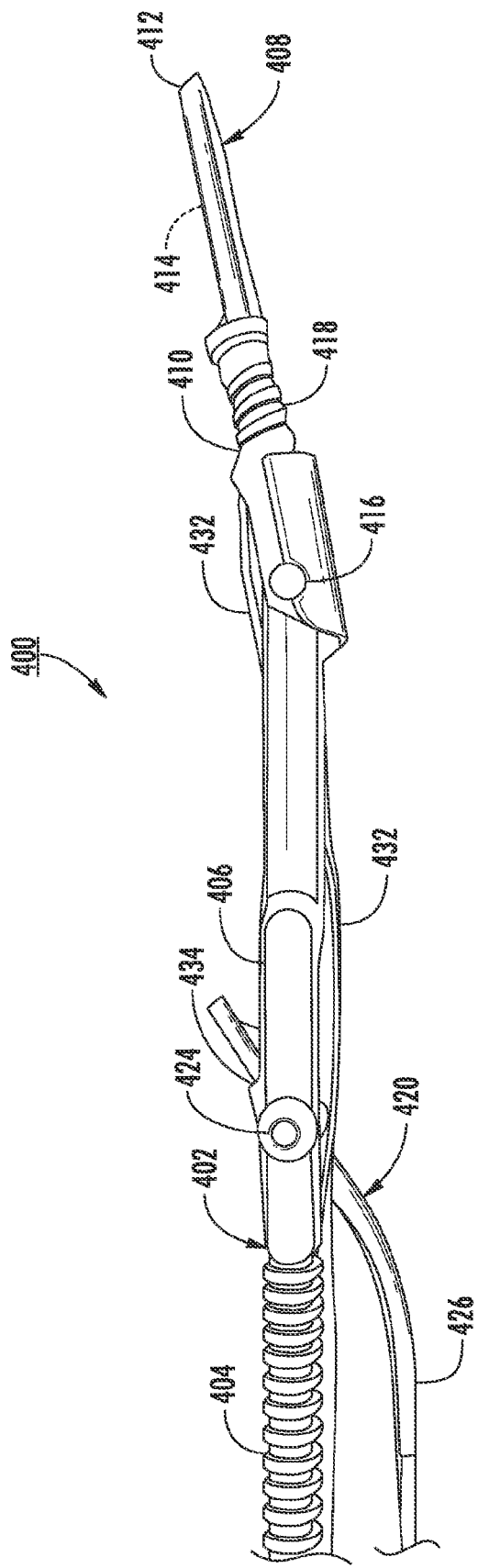
FIG. 35 is a perspective view of another alternative embodiment of a medical device fixation tool in a deployment position.
Figure 36:
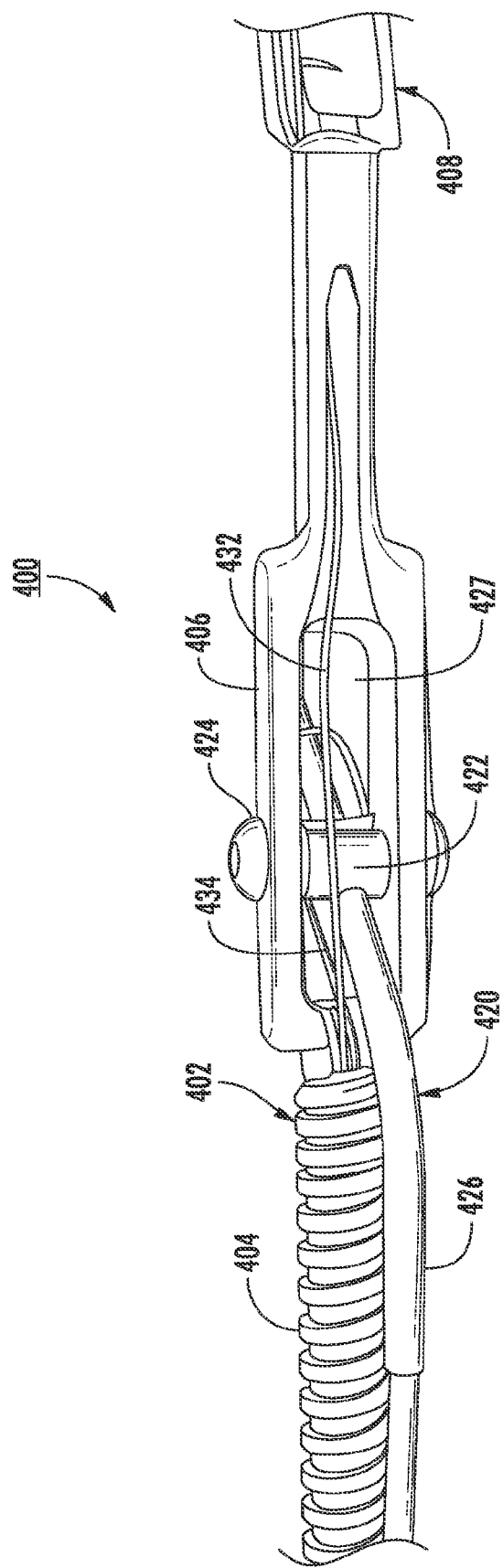
FIG. 36 is a bottom plane view of the medical device fixation tool in FIG. 35.
Figure 37:
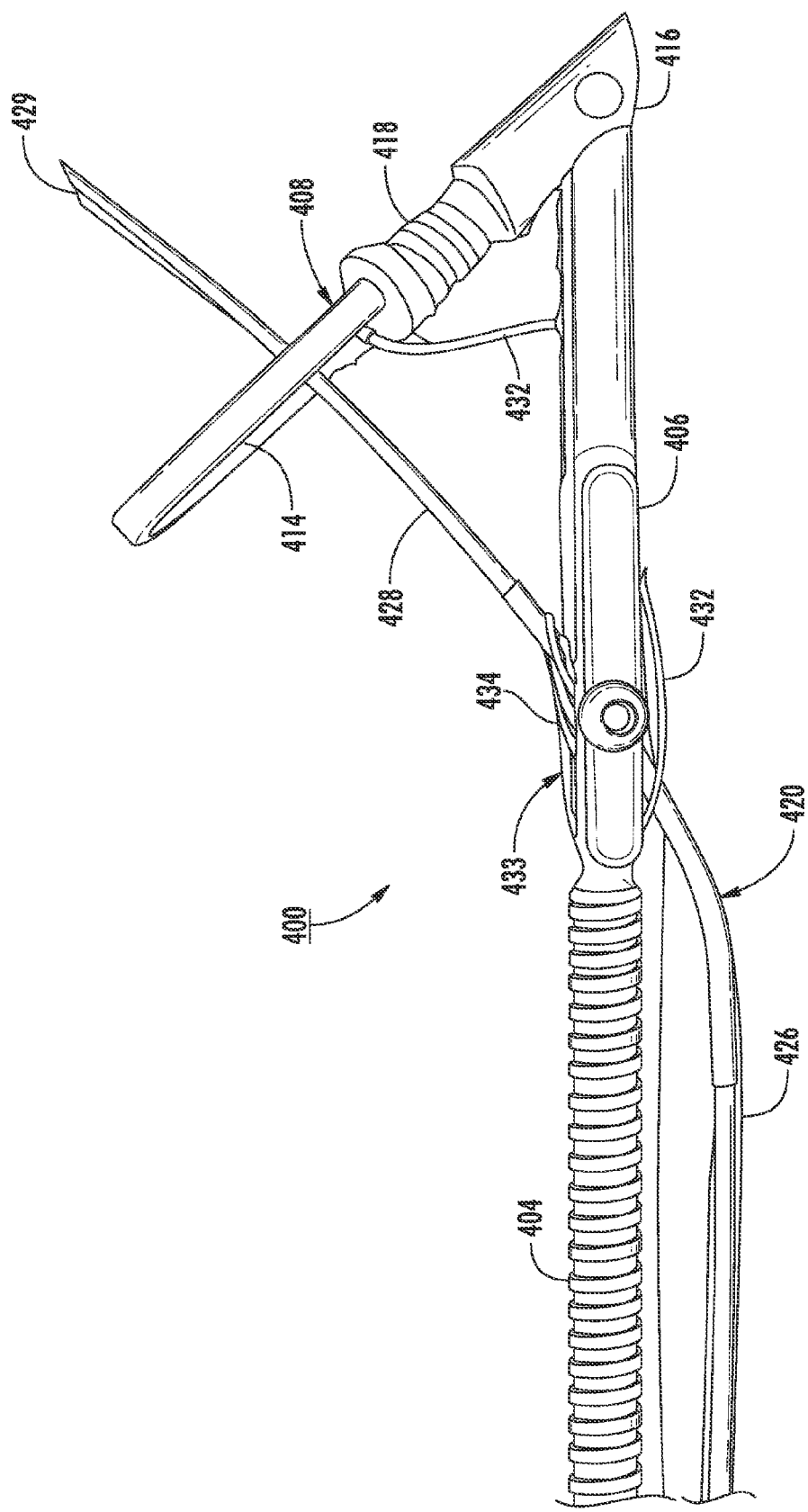
FIG. 37 is the same view as FIG. 35 showing the medical device fixation tool in a use position.

Another alternative embodiment of a medical device fixation tool 400 includes a needle driver, such as a needle pusher assembly 420, and a shaft 402 (FIGS. 35-37). Shaft 402 has a size and configuration to position needle driver 420 within a hollow organ or cavity through a natural orifice. For example, shaft 402 has a length and diameter that is capable of passing through an over-tube positioned in the esophagus and to position needle pusher assembly 420 in the GE region of the recipient of a medical device such as a bariatric device of the type described in International Patent Application Publication No. WO 2008/101048 A2 entitled BARIATRIC DEVICE AND METHOD. Needle pusher assembly 420 is capable of transmitting sufficient force to penetrate the walls of the esophageal and cardiac members of the bariatric device and the intervening tissue.

Shaft 402 has a flexible portion 404 and a more rigid end portion 406. Flexible portion 404 can adapt to various shapes, such as curved paths, to thereby facilitate movement of tool 400 through an over-tube in the natural orifice, such as the esophagus of the recipient of the medical device including natural curvature of the esophagus. Tool 400 includes a support 408 that is pivotally mounted to shaft 402 at end portion 406. Support 408 is pivotal between the deployment position, illustrated in FIG. 35, in which it is generally in line with shaft 402 and a use position, illustrated in FIG. 37, capable of providing support to the medical device as it is penetrated by the needle pusher assembly. Support 408 has a first portion 410 that is pivotally mounted to shaft 402 by a pivot 416. Support 408 further includes a second, outer portion 412 that defines an opening or void 414 that allows needle pusher assembly 420 to pass. A semi-flexible join 418 may be provided between portions 410 and 412 to facilitate flexing of support 408 as it passes through the over-tube during deployment, but allows only limited flexing so that outer portion 412 is sufficiently rigid during use. A support adjustment wire 432 passes through a flexible portion of shaft 404, though opening 427 and attaches to support 408 in order to adjust the position of the support relative to shaft 402. With support 408 biased to an extended position in line with the shaft, such as illustrated in FIG. 35, by a torsion spring, or the like, a pulling force applied to wire 432 will pivot support 408 to the use position, illustrated in FIG. 37. Wire 432 may be actuated by a wire adjustment member 444 (FIG. 38) or other such actuator as would be apparent to the skilled artisan.

Once the medical device is fixed, support adjustment wire 432 can be relaxed to allow support 408 to move to its deployment position in line with shaft 404 for removal from the recipient. Other techniques may be used to assist in maintaining the alignment of support 408 with shaft 402 during deployment of the fixation tool. For example, a small opening could be formed at the distal tip of support 408 and passed over a guide wire that has previously been inserted in the recipient, such as through an over-tube in the natural orifice. The guide wire can be used both to guide medical device fixation tool 400 through the natural orifice as well as to resist support 408 from moving out of line with shaft 402. Also, support 408 may be latched into a position in line with shaft 408, using known techniques, during deployment through the over-tube and released to move into its use position once the fixation tool is in position.

Figure 39:
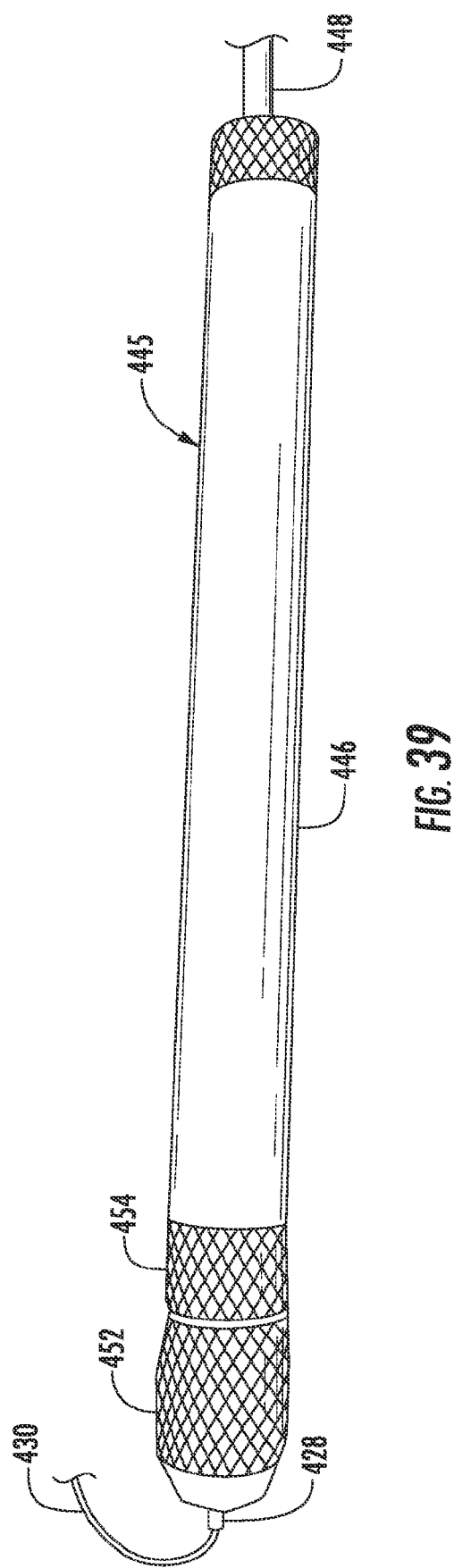
FIG. 39 is a perspective view of a plunger.
Figure 42:
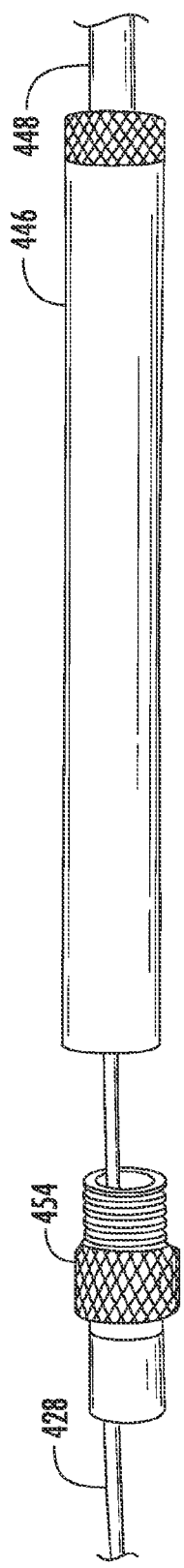
Figure 43:
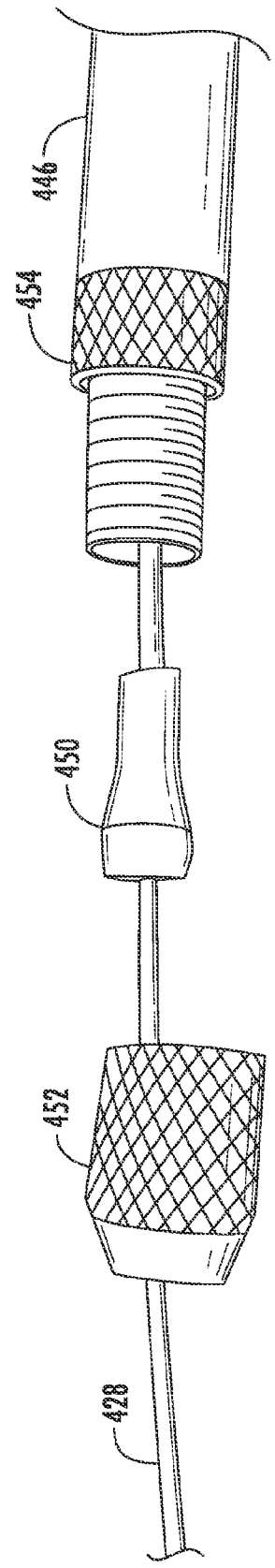
Figure 44:
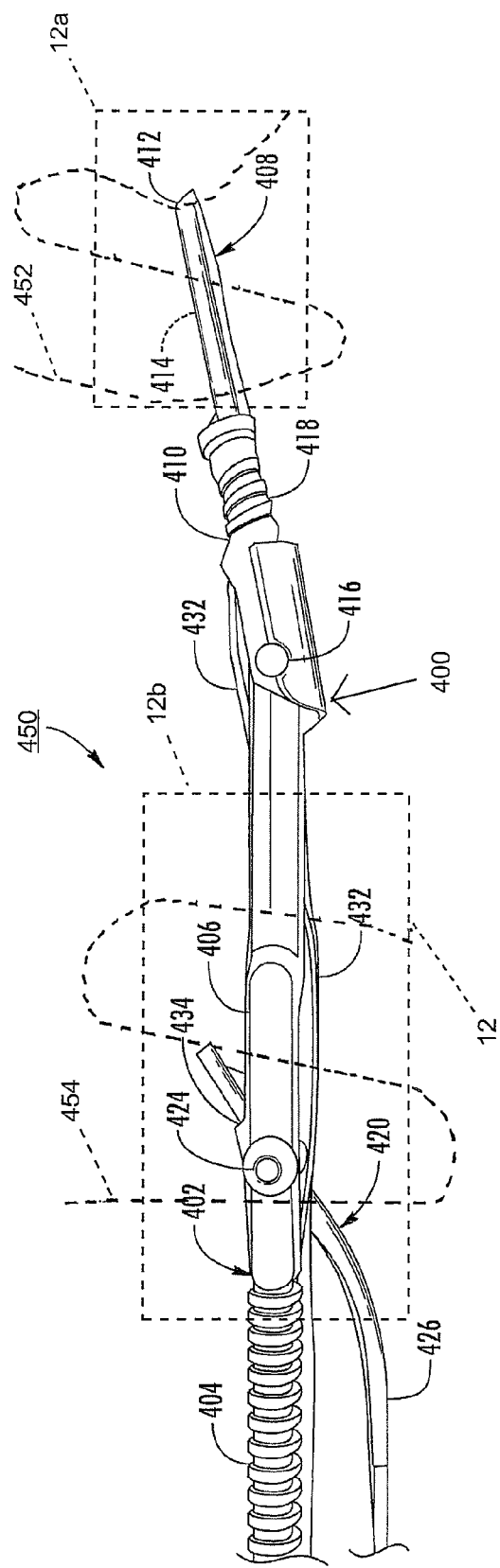
FIG. 44 is the same view as FIG. 35 of a combination fixation tool and medical device.

Needle pusher assembly 420 includes a needle guide in the form of a needle housing 426 that is pivotally mounted distally to end portion 406 of shaft 402 by a pivotally mounted yoke 422. As best seen in FIG. 36, yoke 422 is pivotally mounted in an opening 427 of end portion 406 by a pivot 424. Needle pusher assembly 420 further includes a needle pusher assembly in the form of a needle assembly 428 that is axially moveable within housing 426 between a retracted position illustrated in FIG. 35 and an extended position illustrated in FIG. 37. In the illustrated embodiment, needle assembly 428 is made from a laterally flexible yet longitudinally non-compressible material, such as a Nitinol tube that is ground to a bevel point 429 in a similar fashion as the combination of needle 224 and deployment tube 229 previously described. Needle assembly 428 is hollow having an axial through-passage that houses a T-fastener (not shown, similar to fastener 166 previously described), adjacent point 429, a tether (not shown, similar to tether 62 previously described), extending from the T-fastener and a needle control filament 430 (FIG. 39) that extends out the proximal end of needle assembly 428. Needle control filament 430 is axially moveable by an actuator (not shown) to dislodge the T-fastener distally from the needle assembly after the needle assembly has penetrated the medical device, such as the cardiac member of the bariatric device. Needle housing 426 may be made as a hollow flexible cable, such as from a polymeric tube, such as a polymide tube, with a wire wound around the tube to provide stiffness and abrasion resistance.

Figure 38:
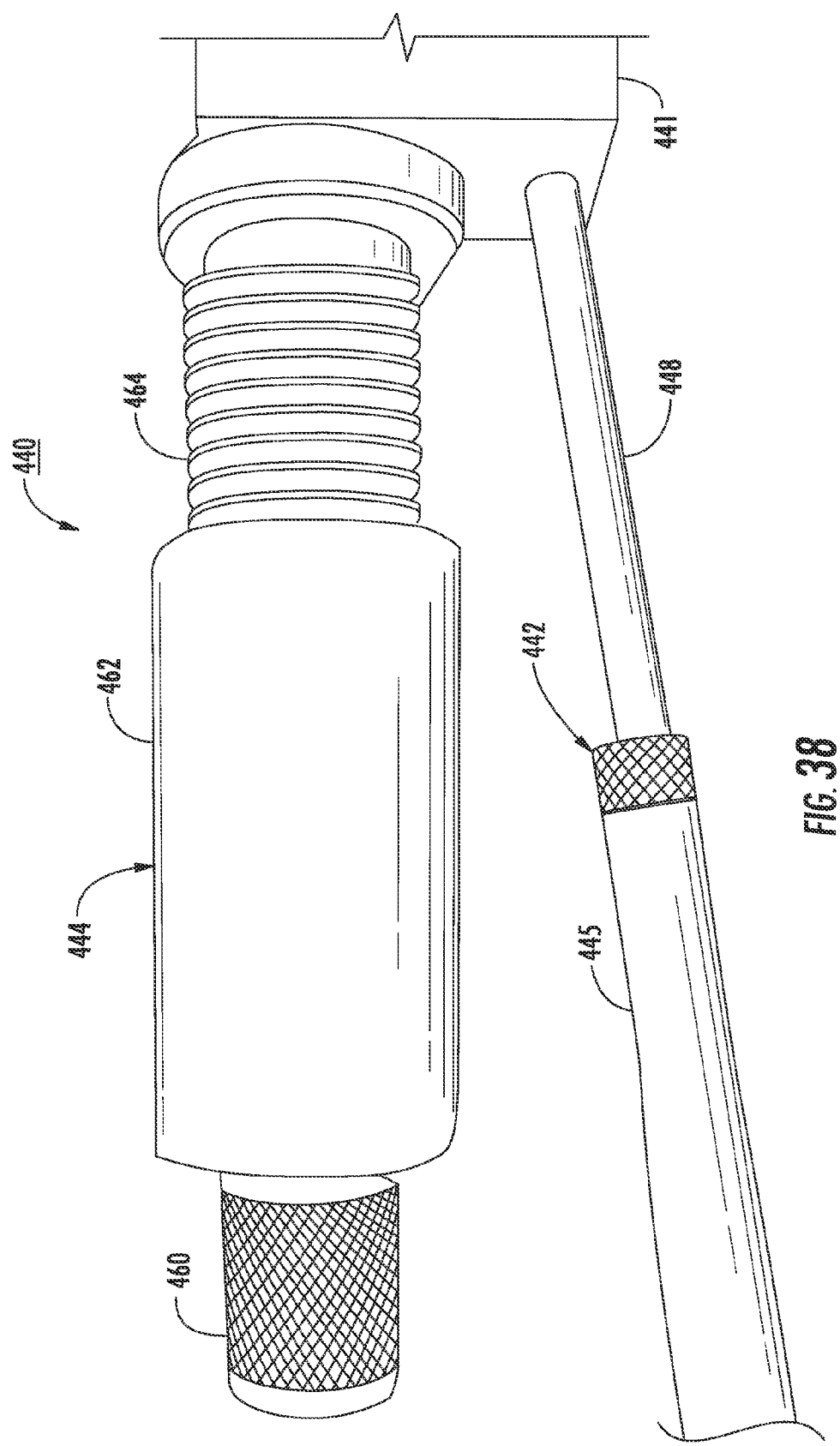
FIG. 38 is a perspective view of an actuator assembly.

Medical device fixation tool 400 includes an aiming device 433 for aiming the needle pusher driver relative to shaft 402. In the illustrative embodiment, aiming device 433 is made up of a wire 434 that is looped around needle housing 426 and extends though shaft 402 to a proximal actuator, such as a wire adjustment member 444 (FIG. 38). Yoke 422 may be spring biased, such as by a torsion spring, or the like, into an orientation (not illustrated) with needle housing 426 close to flexible portion 404. This maintains a small diameter for tool 400 to pass through the natural orifice during deployment. When adjustment member 444 retracts wire 434, the force on needle housing 426 overcomes the biasing force on yoke 422 and pivots the housing to a use position, such as that illustrated in FIGS. 35-37. This aims the needle pusher driver in the direction of void 414. It also allows the physician to steer needle assembly 428 relative to the medical device, as necessary, to properly position the tether. An alternative embodiment of yoke 422 may include a cam surface (not shown) with needle aiming wire 434 passing over the cam surface proximally to its attachment to needle housing 426. This would create a lever effect to thereby increase the amount of torque that could be applied by wire 434 to yoke 422 for a given amount of force applied to the wire, as would be apparent to the skilled artisan. Also, other forms of an aiming device 433, such as a worm gear operated by a rotary shaft, or the like, would be apparent to the skilled artisan.

In the illustrated embodiment, flexible portion 404 is made from a flexible polymer tube, such as of the type available from Kientec Systems, Inc. or MicroLumen. Wires 432 and 434 may be routed through channels or tubes formed, such as from Nitinol tubes within shaft 402 or along the shaft. For particular applications, such as a reusable medical device fixation tool, an outer cover may be applied to flexible portion 404 to add durability and to increase smoothness. It should be apparent to the skilled artisan that the medical device fixation tool described herein can be made as a single-use device. The medical device fixation tool 400 can also be combined with the medical device to provide a combination fixation tool and medical device 450 in order to both deploy and fix the medical device within a body cavity through a natural orifice. In the case of a bariatric device 12, the cardiac member 12a could be compressed in proper orientation with respect to support 408 with the esophageal member 12b around shaft 402. Cardiac member 12a can be held in a compressed state with a wire or other filament 452 wound around the cardiac member 12a. Esophageal member 12b can be held in a compressed state with a wire or other filament 454 wound around esophageal member 12b. Once the combination fixation tool and bariatric device 450 is properly positioned within the recipient, the filaments 452 and 454 holding the bariatric device members 12a, 12b in their compressed states and can be the members 12a, 12b to expand to their deployed state. Because the fixation tool 400 is already aligned with the bariatric device, the support 408 can be actuated to its use position and the needle guide 426 actuated to its aimed position to apply the tether(s). However, the medical device could be deployed separately from the fixation tool, if desired.

While various actuators may be used to operate needle pusher assembly 420, support adjustment wire 432, and needle aiming wire 434, medical device fixation tool 400 may include an actuator assembly 440 that is illustrated in FIGS. 38-43. Actuator assembly 440 may include a needle deployment actuator 442 that is attached to a base 441 affixed proximally to shaft 402. Needle deployment actuator 442 includes an extension 448 of base 441 and a plunger 445 that is moveable with respect to extension 448. Needle deployment actuator 442 may be configured to limit movement of needle assembly 428. This reduces the likelihood of needle assembly 428 inadvertently rupturing needle housing 426 by being retracted too far into the housing.

Referring to drawing FIGS. 38-43, needle deployment actuator 442 includes a plunger 445 having a barrel 446 that moves linearly with respect to extension 448. One end of barrel 446 grasps needle assembly 428 via a clamp 450 and a knurled nut 452 that tightens clamp 450 to needle assembly 428 when nut 452 engages mating threads on an adapter 454 that threads into barrel 446. The other end of barrel 446 is restrained for limited motion with respect to extension 448. This is accomplished by a threaded stop 456 that holds another knurled nut 458 for limited sliding motion with respect to extension 448. Knurled nut 458 threads into barrel 446. In addition to limiting movement of plunger 445, and, hence, needle assembly 428, the components of the needle deployment actuator 442 can be disassembled to allow for cleaning and sterilization as needed.

Actuator assembly 440 may further include separate wire adjustment members 444 for longitudinally displacing wires 432 and 434, although only one wire adjustment member 444 is illustrated. Member 444 includes a clasp 460 that grasps a proximal end of a wire 432, 434 and a rotary knob 462 attached to clasp 460. Knob 462 is threadably engaged with a threaded tube 464 that extends from base 441. As knob 462 is rotated, the large threads between the knob and tube 464 provide fine movement of the respective wires 430, 432.

Although various embodiments are illustrated herein, it should be understood that the features disclosed in each embodiment may be combined as would be apparent to the skilled artisan. Changes and modifications in the specifically described embodiments can be carried out without departing from the principles of the invention which is intended to be limited only by the scope of the appended claims, as interpreted according to the principles of patent law including the doctrine of equivalents.

The embodiments of the invention in which an exclusive property or privilege is claimed are defined as follows:

1. A medical device fixation tool assembly that is adapted to fix a medical device within a hollow organ or cavity through a natural orifice, said medical device fixation tool assembly comprising:

a medical device fixation tool and a medical device positioned on said tool, said medical device configured to the size and shape of the hollow organ or cavity, wherein said tool is adapted to both deploy and fix said medical device in the hollow organ or cavity;

said tool comprising a needle driver, a shaft and a support, said needle driver comprising at least one needle and a needle guide that is adapted to receive said at least one needle, wherein said at least one needle comprises a unitary needle assembly comprising a tubular member having a sharpened end portion, wherein said needle assembly is adapted to deploy a fastener attached to a tether, wherein said needle driver is adapted to transmit a force to the at least one needle to penetrate a portion of said medical device;

said shaft being elongated and adapted to position at least a portion of said needle driver at the hollow organ or cavity through the natural orifice;

said needle guide having a terminal portion wherein said at least one needle exits said needle guide to deliver said at least one needle to said portion of said medical device and a proximal portion that is proximal said terminal portion, said needle guide transversing said shaft wherein said proximal portion thereof is on one side of said shaft and said terminal portion is on an opposite side of said shaft that is opposite said one side in order to transmit the force to the at least one needle that is sufficient to penetrate said portion of said medical device;

wherein said support is adapted to resist distal movement of said portion of said medical device in response to the force of the at least one needle penetrating said portion of the said medical device; and a fastener deployment filament that is adapted to move relative to said needle assembly to deploy the fastener.

2. The medical device fixation tool assembly as claimed in claim 1, wherein said proximal portion of said needle guide is curved.

3. The medical device fixation tool assembly as claimed in claim 1, wherein said proximal portion of said needle guide is at least partially spaced from said shaft.

4. The medical device fixation tool assembly as claimed in claim 1, wherein said support is positioned on said shaft spaced from said terminal portion of said needle guide.

5. The medical device fixation tool assembly as claimed in claim 1, wherein said needle driver is adapted to transmit a sufficient force to the at least one needle to penetrate at least two portions of the medical device, wherein each of said portions of the medical device has a greater puncture resistance than a mammalian tissue.

6. The medical device fixation tool assembly as claimed in claim 1, wherein said shaft comprises a flexible shaft portion.

7. A medical device fixation tool assembly that is adapted to fix a medical device within a hollow organ or cavity through a natural orifice, said medical device fixation tool assembly comprising:

a medical device fixation tool and a medical device positioned on said tool, said medical device configured to the size and shape of the hollow organ or cavity, wherein said tool is adapted to both deploy and fix said medical device in the hollow organ or cavity;

said tool comprising a needle driver, a shaft and a support, said needle driver comprising at least one needle and a needle guide that is adapted to receive said at least one needle, wherein said needle driver is adapted to transmit a force to the at least one needle that is sufficient to penetrate a portion of said medical device;

said shaft elongated and adapted to position at least a portion of said needle driver at the hollow organ or cavity through the natural orifice;

said needle guide having a terminal portion wherein said at least one needle exits said needle guide to deliver said at least one needle to said portion of said medical device and a proximal portion that is proximal said terminal portion;

wherein said support is adapted to resist distal movement of said portion of said medical device in response to the force of the at least one needle penetrating said portion of said medical device, wherein said support has a use position that is angled from a central axis of a shaft; and a needle aiming device, wherein said needle guide is moveable relative to said shaft with said aiming device.

8. The medical device fixation tool assembly as claimed in claim 7, wherein said needle guide transverses said shaft wherein said proximal portion thereof is on one side of said shaft and said terminal portion is on an opposite side of said shaft that is opposite said one side and wherein said proximal portion of said needle guide is at least partially spaced from said shaft.

9. The medical device fixation tool assembly as claimed in claim 7, wherein said proximal portion of said needle guide is curved.

10. The medical device fixation tool assembly as claimed in claim 7, wherein said needle guide includes a rotatable yoke fixed to said shaft, a needle housing fixed to said yoke, and a wire operatively associated with said shaft and said housing to selectively move said needle housing relative to said shaft.

11. The medical device fixation tool assembly as claimed in claim 7, wherein said at least one needle comprises a unitary needle assembly comprising a tubular member having a sharpened end portion.

12. The medical device fixation tool assembly as claimed in claim 11 including a needle driver actuator for said needle assembly, said actuator restricting the range of motion of said needle assembly.

13. The medical device fixation tool assembly as claimed in claim 11, wherein said needle assembly is adapted to deploy a fastener attached to a tether.

14. A medical device fixation tool assembly that is adapted to fix a medical device within a hollow organ or cavity through a natural orifice, said medical device fixation tool assembly comprising:

a medical device fixation tool and a medical device positioned on said tool, said medical device configured to the size and shape of the hollow organ or cavity, wherein said tool is adapted to both deploy and fix said medical device in the hollow organ or cavity;

said tool comprising a needle driver, a shaft and a support, said needle driver comprising at least one needle and a needle guide that is adapted to receive said at least one needle, wherein said at least one needle comprises a unitary needle assembly comprising a tubular member having a sharpened end portion, wherein said needle assembly is adapted to deploy a fastener attached to a tether, wherein said needle driver is adapted to transmit a force to the at least one needle that is sufficient to penetrate a portion of said medical device;

said shaft elongated and adapted to position at least a portion of said needle driver at the hollow organ or cavity through the natural orifice;

said needle guide having a terminal portion wherein said at least one needle exits said needle guide to deliver said at least one needle to said portion of said medical device and a proximal portion that is proximal said terminal portion;

wherein said support is adapted to resist distal movement of said portion of said medical device in response to the force of the at least one needle penetrating said portion of said medical device, wherein said support has a use position that is angled from a central axis of said shaft; and a fastener deployment filament that is adapted to move relative to said needle assembly to deploy the fastener.

15. The medical device fixation tool assembly as claimed in claim 14 including a needle aiming device, wherein said needle guide is moveable relative to said shaft with said aiming device.

16. The medical device fixation tool assembly as claimed in claim 15, wherein said needle guide includes a rotatable yoke fixed to said shaft, a needle housing fixed to said yoke, and a wire operatively associated with said shaft and said housing to selectively move said needle housing relative to said shaft.

17. The medical device fixation tool assembly as claimed in claim 14, wherein said support is positioned on said shaft spaced from said terminal portion of said needle guide.

18. The medical device fixation tool assembly as claimed in claim 14, wherein said needle driver is adapted to transmit a sufficient force to the at least one needle to penetrate at least two portions of the medical device, wherein each of said portions of the medical device has a greater puncture resistance than a mammalian tissue.

19. The medical device fixation tool assembly as claimed in claim 14, wherein said shaft comprises a flexible shaft portion.

20. A medical device fixation tool assembly that is adapted to fix a medical device within a hollow organ or cavity through a natural orifice, said medical device fixation tool assembly comprising:
a medical device fixation tool and a medical device compressed to said tool, said medical device configured to the size and shape of the hollow organ or cavity, wherein said tool is adapted to both deploy and fix said medical device in the hollow organ or cavity;
said tool comprising a needle driver, a shaft and a support, said needle driver comprising at least one needle and a needle guide that is adapted to receive said at least one needle, wherein said needle driver is adapted to transmit a force to the at least one needle that is sufficient to penetrate a portion of said medical device;
said shaft elongated and adapted to position at least a portion of said needle driver at the hollow organ or cavity through the natural orifice;
said needle guide having a terminal portion wherein said at least one needle exits said needle guide to deliver said at least one needle to said portion of said medical device and a proximal portion that is proximal said terminal portion; and
wherein said support is adapted to resist distal movement of said portion of said medical device in response to the force of the at least one needle penetrating said portion of said medical device, wherein said support has a use position that is angled from a central axis of said shaft, wherein said medical device comprises first and second members, each is compressed with at a filament wound around that one of said first and second members, wherein pulling on said filament releases that one of said first and second members of said medical device from being compressed.

21. The medical device fixation tool assembly as claimed in claim 20, wherein said at least one needle comprises a unitary needle assembly comprising a tubular member having a sharpened end portion.

22. The medical device fixation tool assembly as claimed in claim 21 including a needle driver actuator for said needle assembly, said actuator restricting the range of motion of said needle assembly.

23. The medical device fixation tool assembly as claimed in claim 21, wherein said needle assembly is adapted to deploy a fastener attached to a tether.

24. A medical device fixation tool assembly that is adapted to fix a medical device within a hollow organ or cavity through a natural orifice, said medical device fixation tool assembly comprising:
a medical device fixation tool and a medical device compressed to said tool, said medical device configured to the size and shape of the hollow organ or cavity, wherein said tool is adapted to both deploy and fix said medical device in the hollow organ or cavity;
said tool comprising a needle driver, a shaft and a support, said needle driver comprising at least one needle and a needle guide that is adapted to receive said at least one needle, wherein said needle driver is adapted to transmit a force to the at least one needle to penetrate a portion of said medical device;
said shaft being elongated and adapted to position at least a portion of said needle driver at the hollow organ or cavity through the natural orifice;
said needle guide having a terminal portion wherein said at least one needle exits said needle guide to deliver said at least one needle to said portion of said medical device and a proximal portion that is proximal said terminal portion, said needle guide transversing said shaft wherein said proximal portion thereof is on one side of said shaft and said terminal portion is on an opposite side of said shaft that is opposite said one side in order to transmit the force to the at least one needle that is sufficient to penetrate said portion of said medical device; and
wherein said support is adapted to resist distal movement of said portion of said medical device in response to the force of the at least one needle penetrating said portion of the said medical device;
wherein said medical device comprises first and second members, said first member compressed to said shaft with a filament wound around said first member wherein pulling on said filament releases said first member from being compressed and said second member compressed to said support with another filament wound around said second member wherein pulling on said another filament releases said second member from being compressed.

25. A medical device fixation tool assembly that is adapted to fix a medical device within a hollow organ or cavity through a natural orifice, said medical device fixation tool assembly comprising:
a medical device fixation tool and a medical device compressed to said tool, said medical device configured to the size and shape of the hollow organ or cavity, wherein said tool is adapted to both deploy and fix said medical device in the hollow organ or cavity;
said tool comprising a needle driver, a shaft and a support;
wherein said needle driver is adapted to receive at least one needle and to transmit a force to said at least one needle that is sufficient to penetrate a portion of said medical device;
wherein said shaft is adapted to position at least a portion of said needle driver at the hollow organ or cavity through the natural orifice;
wherein said support is adapted to resist distal movement of said portion of said medical device in response to the force of said at least one needle penetrating said portion of said medical device; and
wherein said medical device comprises first and second members, said first member compressed to said shaft with a filament wound around said first member wherein pulling on said filament releases said first member from being compressed and said second member compressed to said support with another filament wound around said second member wherein pulling on said another filament releases said second member from being compressed.

26. The medical device fixation tool assembly as claimed in claim 25, wherein said needle driver comprising at least one needle and a needle guide that is adapted to receive said at least one needle to deliver said at least one needle to said portion of said medical device.

27. The medical device fixation tool assembly as claimed in claim 25, wherein said support further defines a first portion and a second portion, said first portion being adjacent said shaft, said second portion defining a void, wherein said second portion is moveable from a deployment position to a use position, wherein said void is substantially aligned with said needle driver in said use position.

28. The medical device fixation tool assembly as claimed in claim 27 wherein said second portion is substantially aligned with said shaft in said deployment position.

29. The medical device fixation tool assembly as claimed in claim 26 wherein said support is pivotally supported at said shaft.

30. The medical device fixation tool assembly as claimed in claim 26 wherein said support is adapted to extend from said shaft to substantially align with said shaft in said deployment position.

31. The medical device fixation tool assembly as claimed in claim 25, wherein said needle driver is adapted to transmit a sufficient force to the at least one needle to penetrate at least two portions of the medical device, wherein each of said portions of the medical device has a greater puncture resistance than a mammalian tissue.

* * * * *

UNITED STATES PATENT AND TRADEMARK OFFICE
CERTIFICATE OF CORRECTION

PATENT NO.         : 8,372,087 B2
APPLICATION NO.    : 12/541567
DATED              : February 12, 2013
INVENTOR(S)        : Randal S. Baker et al.

Page 1 of 1

It is certified that error appears in the above-identified patent and that said Letters Patent is hereby corrected as shown below:

In the Specification

Column 11
Line 46, insert --pulled in order to release the-- after "can be"

In the Claims

Column 15
Line 30, Claim 20, delete "at" after "with"

Column 17
Line 8, Claim 30, "26" should be --28--

Signed and Sealed this
Eleventh Day of February, 2014

Michelle K. Lee
*Deputy Director of the United States Patent and Trademark Office*